United States Patent
Diep et al.

(10) Patent No.: US 9,611,293 B2
(45) Date of Patent: Apr. 4, 2017

(54) SYNTHESIS OF BETA-ARRESTIN EFFECTORS

(71) Applicant: Trevena, Inc., King of Prussia, PA (US)

(72) Inventors: Nhut K. Diep, Farmingville, NY (US); Yuriy Kalyan, Staten Island, NY (US); Graham Lawton, Smithtown, NY (US); Matthew Ronsheim, Port Jefferson, NY (US); Shao Hong Zhou, Commack, NY (US); Saibaba Racha, Smithown, NY (US)

(73) Assignee: Trevena, Inc., King of Prussia, PA (US)

(*) Notice: Subject to any disclaimer, the term of this patent is extended or adjusted under 35 U.S.C. 154(b) by 0 days.

(21) Appl. No.: 14/715,595

(22) Filed: May 19, 2015

(65) Prior Publication Data

US 2015/0329593 A1    Nov. 19, 2015

Related U.S. Application Data

(60) Provisional application No. 62/000,329, filed on May 19, 2014.

(51) Int. Cl.
| | | |
|---|---|---|
| A61K 38/04 | (2006.01) |
| C07K 5/00 | (2006.01) |
| C07K 7/00 | (2006.01) |
| C07K 16/00 | (2006.01) |
| C07K 17/00 | (2006.01) |
| C07K 7/06 | (2006.01) |
| A61K 38/00 | (2006.01) |

(52) U.S. Cl.
CPC .......... *C07K 7/06* (2013.01); *A61K 38/00* (2013.01)

(58) Field of Classification Search
CPC ...... A61K 38/00; A61K 38/085; A61K 51/08; A61K 38/08
See application file for complete search history.

(56) References Cited

U.S. PATENT DOCUMENTS

| | | |
|---|---|---|
| 3,751,404 A | 8/1973 | Sipos et al. |
| 3,932,624 A | 1/1976 | Fulton |
| 3,960,830 A | 6/1976 | Bayer et al. |
| 4,115,538 A | 9/1978 | Satoh et al. |
| 4,298,523 A | 11/1981 | Heavner |
| 4,547,489 A | 10/1985 | Goldstein et al. |
| 5,112,807 A | 5/1992 | Hamano et al. |
| 5,182,264 A | 1/1993 | Watkins |
| 5,436,128 A | 7/1995 | Harpold et al. |
| 5,629,292 A | 5/1997 | Rodgers et al. |
| 5,889,020 A | 3/1999 | Huxley et al. |
| 8,486,885 B2 | 7/2013 | Yamashita et al. |
| 8,796,204 B2 | 8/2014 | Yamashita et al. |
| 8,809,260 B2 | 8/2014 | Yamashita et al. |
| 2003/0017970 A1 | 1/2003 | Rodgers et al. |
| 2004/0214836 A1 | 10/2004 | Cheresh et al. |
| 2005/0202029 A1 | 9/2005 | Zabel et al. |
| 2007/0286863 A1 | 12/2007 | Sinal et al. |
| 2009/0280113 A1 | 11/2009 | Graham et al. |
| 2010/0092974 A1 | 4/2010 | Zabel et al. |
| 2010/0150990 A1 | 6/2010 | Greaves et al. |
| 2010/0184701 A1 | 7/2010 | Yamashita et al. |

FOREIGN PATENT DOCUMENTS

| | | |
|---|---|---|
| EP | 498361 A2 | 8/1992 |
| WO | 9003181 A2 | 4/1990 |
| WO | 9203145 A1 | 3/1992 |
| WO | 9213564 A1 | 8/1992 |
| WO | 9614858 A1 | 5/1996 |
| WO | 9963930 A2 | 12/1999 |
| WO | 2008018792 A2 | 2/2008 |
| WO | 2009137465 A2 | 11/2009 |
| WO | 2010077339 A2 | 7/2010 |
| WO | 2011035332 A1 | 3/2011 |
| WO | 2011163619 A1 | 12/2011 |
| WO | 2012150890 A1 | 11/2012 |

OTHER PUBLICATIONS

Paul et al., Stereochemically constrained peptides. Theoretical and experimental studies on the conformations of peptides containing 1-aminocyclohexanecarboxylic acid, Journal of the American Chemcical Society 1986 108 (20):6363-6370.

Samanen et al, Effects of d-amino acid substitution on antagonist activities of angiotensin II analogues, Journal of Medicinal Chemistry, 1998 31:510-516.

Samanen et al. "An investigation of angiotensin II agonist and antagonist analogs with 5,5-dimethylthiazolidine-4-carboxylic acid and other constrained amino acids", J. Medicinal Chemistry, 1991, 34, 3036-3043.

Samanen et al. "Potent angiotensin II antagonists with non-beta-branched amino acids in position 5", J. Medicinal Chemistry, 1989, 32, 466-472.

Sasaki et al., "Solid phase synthesis of peptides containing the CH2NH peptide bond isostere," Peptides (1987) 8(1):119-121.

Schoelkens, B.A. et al., "1 ,8 Disubstituted analogues of [Ile<5>] and [Val<5>] angiotensin II: difference in potency and specificity of angiotensin II antagonistic activity", Hoppe-Seyler's Zeitschrift Fur Physiologische Chemie, 1976, 357:825-838.

Seitter et al., "Analysis for protein modifications and nonprotein cofactors.," Meth Enzymol (1990) 182:626-646.

Sell et al., "Chemerin is a novel adipocyte-derived factor inducing insulin resistance in primary human skeletal muscle cells," Diabetes (2009) 58(12):2731-2740.

Shimamura et al., "Identification of a stable chemerin analog with potent activity toward ChemR23," Peptides (2009) 30:1529-1538.

Siegal et al., "The nature of the principal type 1 interferon-producing cells in human blood," Science (1999) 284 (5421): 1835-1837.

Smith et al., Tritiated D-ala1-peptide T binding: A pharmacologic basis for the design of drugs which inhibit HIV receptor binding, Drug Development Res (1988) 15:371-379.

Sozzani et al., "Trafficking properties of plasmacytoid dendritic cells in health and disease," Trends in Immunology (2010) 31:270-277.

(Continued)

Primary Examiner — James H Alstrum Acevedo
Assistant Examiner — Kaipeen Yang
(74) Attorney, Agent, or Firm — Pepper Hamilton LLP

(57) ABSTRACT

Embodiments disclosed herein provide compounds and methods for preparing Beta-Arrestin Effectors.

12 Claims, 3 Drawing Sheets

(56) References Cited

OTHER PUBLICATIONS

Spyroulias et al., Comparison of the solution structures of angiotensin I & II: implication for structure-function relationship, Eur J Biochem 2003 270(10):2163-73.

Traynor et al., "Modulation by mu-opioid agonists of guanosine-5'-0-(3-[35S]thio)triphosphate binding to membranes from human neuroblastoma SH-SY5Y cells," Mol Pharmacal (1995) 47(4):848-854.

Vestergarrd-Bogind et al., "Single-file diffusion through the Ca2+-activated K+ channel of human red cells" J Membrane Bio (1985) 88(1):67-75.

Violin et al, Selectively engaging b-arrestins at the angiotensin II type 1 receptor reduces blood pressure and increases cardiac performance, J Pharm Exp Thera 2010 335(3):572-579.

Violin, J. et al., "Beta-arrestin-biased ligands at seven-transmembrane receptors." Trends Pharmacal Sci., 2007, 28(8):416-422.

Vrecl et al., "Agonist-induced endocytosis and recycling of the gonadotropin-releasing hormone receptor: effect of beta-arrestin on internalization kinetics," Mol Endocrinol (1996) 12:1818-1829.

Wilkie et al., "Characterization of G-protein alpha subunits in the Gq class: expression in murine tissues and in stromal and hematopoietic cell lines," Proc Nat'l Acad Sci USA (1991) 88(22):10049-10053.

Wittamer et al., "Specific recruitment of antigen-presenting cells by chemerin, a novel processed ligand from human inflammatory fluids," Journal of Experimental Medicine (2003) 198(7):977-985.

Wittamer et al., "The C-terminal nonapeptide of mature chemerin activates the chemerin receptor with low nanomolar potency," Journal of Biological Chemistry (2004) 279(11):9956-9962.

Wollenberg et al., "Plasmacytoid dendritic cells: a new cutaneous dendritic cell subset with distinct role in inflammatory skin diseases," Journal of Investigative Dermatology (2002) 119(5): 1096-1102.

Zabel et al., "Chemokine-like receptor 1 expression and chemerin-directed chemotaxis distinguish plasmacytoid from myeloid dendritic cells in human blood," Journal of Immunology (2010) 174:244-251.

Zabel et al., "Chemokine-like receptor 1 expression by macrophages in vivo: regulation by TGF-beta and TLR ligands," Experimental Hematology (2006) 34(8): 1106-1114.

Non-final Office Action dated Aug. 27, 2015 in related U.S. Appl. No. 14/461,081.

Non-Final Office Action dated Jun. 20, 2016 in U.S. Appl. No. 14/631,461.

Gavras, Hospital Chronicles 2008 3(3):100-101.

Khosla, Journal of Medicinal Chemistry 1977 20(8).

"MHRA", Losartan Potassium, PL 19364/0012-14 2008.

"Pharmacology", downloaded online on Jun. 10, 2016 from https://cramberry.net/sets/35114-pharmacology.

Ackerman et al., "Ion channels—basic science and clinical disease," New Eng J Med (1997) 336(22):1575-1595.

Aumelas, A. et al., "Studies on Angiotensin II and Analogs: Impact of Substitution in Position 8 on Conformation and Activity", Proc. Natl. Acad. Sci., 1985, 82:1881-1885.

Barak et al., "Internal trafficking and surface mobility of a functionally intact beta2-adrenergic receptor-green fluorescent protein conjugate," Mol Pharmacal (1997) 51 (2):177-184.

Barnea et al., "The genetic design of signaling cascades to record receptor activation," PNAS (2008) 105(1):64-69.

Berridge et al., "Inositol trisphosphate, a novel second messenger in cellular signal transduction," Nature (1984) 312(5992):315-321.

Bohn et al., "Mu-opioid receptor desensitization by beta-arrestin-2 determines morphine tolerance but not dependence," Nature (2000) 408(6813):720-723.

Bourne et al., "The GTPase superfamily: a conserved switch for diverse cell functions," Nature (1990) 348 (6297): 125-132.

Bourne et al., "The GTPase superfamily: conserved structure and molecular mechanism," Nature (1991) 349 (6305):117-127.

Carpenter et al., The octapeptide angiotensin II adopts a well-defined structure in a phospholipid environment, Eur J Biochem 1998 251(1-2):448-53.

Cash et al., "Synthetic chemerin-derived peptides suppress inflammation through ChemR23," Journal of Experimental Medicine (2008) 2005(4):767-775.

Conway et al, "Quantitative analysis of agonist-dependent parathyroid hormone receptor trafficking in whole cells using a functional green fluorescent protein conjugate," J Cell Physiol (2001) 189(3):341-355.

Daniel et al., "Screening for potassium channel modulators by a high through-put 86-rubidium efflux assay in a 96-well microtiter plate," J Pharmacal Meth (1991) 25(3): 185-193.

Dell'Italia, L., "Translational success stories: angiotensin receptor 1 antagonists in heart failure", Circ Res., 2011, 109(4): 437-452.

DeWire, S. et al., "Biased ligands for better cardiovascular drugs: dissecting G-protein-coupled receptor pharmacology", Circ Res., 2011, 109(2):205-216.

Ernst et al., "Chemerin: at the crossroads of inflammation and obesity," Cell (2010) pp. 1-8.

Fehrentz et al., "An efficient synthesis of optically active alpha-(t-Butoxycarbonylamino)-aldehydes from alpha-amino acids," Synthesis (1983) pp. 676-678.

Felley-Bosco et al., "Constitutive expression of inducible nitric oxide synthase in human bronchial epithelial cells induces c-fos and stimulates the cGMP pathway," Am J Resp Cell and Mol Bio (1994) 11 (2):159-164.

Fukamizu et al., Structure and expression of the human angiotensinogen gene: identification of a unique and highly active promoter, J Biol Chem 1990 265(13):7576-82.

Gantz et al., "Molecular cloning of a novel receptio (CMKLR1) with homology to the chemotactic factor receptors," Cytogenet Cell Genet (1996) 74 (4):286-290.

Gonzales et al., "Improved indicators of cell membrane potential that use fluorescence resonance energy transfer," Chern Bioi (1997) 4(4):269-277.

Goldsmith et al., Angiotensin II and sympathetic activity in patients with congestive heart failure, J Am Coll Cardiol 1993 21(5):1107-13.

Groarke et al., "Visualization of agonist-induced association and trafficking of green fluorescent protein-tagged forms o both beta-arrestin-1 and the thyrotropin-releasing hormone receptor-1 ," J Bio Chern (1999) 274(33):23263-23269.

Hall et al, Angiotensin analogs: The influence of sarcosine substituted in position 1, J Pharmacal Exp Ther. Jan. 1974;188(1):222-8.

Hamill et al., "Improved patch-clamp techniques for high-resolution current recording from cells and cell-free membrane patches," PFiugers Archiv (1981) 391(2):85-100.

Holevinsky et al., "ATP-sensitive K+ channel opener acts as a potent Cl– channel inhibitor in vascular smooth muscle cells," J Membrane Biology (1994) 137(1):57-70.

Jorgensen et. al., Angiotensin II Analogs 7. Stereochemical Factors in the 5 Position Influencing Pressor Activity, Journal of Medicinal Chemistry 1971 14(10).

Kenakin, T ., "Functional selectivity and biased receptor signaling", J Pharmacal Exp Ther., 2011, 336{2):296-302.

Kroeger et al., "Constitutive and agonist-dependent homo-oligomerization of the thyrotropin-releasing hormone receptor. Detection in living cells using bioluminescence resonance energy transfer," J Bioi Chern (2001) 276(16):12736-12743.

Lage et al., Angiotensin II contributes to arteria lcompliance in congestive heart failure, Am J Physiol Heat Circ Physiol 2002 283(4):H1424-29.

Luangsay et al., "Mouse ChemR23 is expressed in dendritic cell subsets and macrophages, and mediates an anti-inflammatory activity of chemerin in a lung disease model," Journal of Immunology (2009) 183:6489-6499.

Meder et al., "Characterization of human circulating TIG2 as a ligand for the orphan receptor ChemR23," FEBS Letters (2003) 555(3):495-499.

Merrifield et al., "Solid Phase Peptide Synthesis. I. The Synthesis of a Tetrapeptide," J Am Chern Soc. (1963) 85(14):2149.

(56) References Cited

OTHER PUBLICATIONS

Mistili et al., "Applications of the green fluorescent protein in cell biology and biotechnology", Nature Biotechnology (1997) 15(10):961-964.
Non-Final Office Action received in related U.S. Appl. No. 12/647,810 dated Jun. 7, 2012.
Non-Final Office Action received in related U.S. Appl. No. 12/647,810 dated Oct. 24, 2012.
Non-Final Office Action received in related U.S. Appl. No. 13/755,637 dated Oct. 15, 2013.
Non-Final Office Action received in related U.S. Appl. No. 13/925,170 dated Dec. 2, 2013.
Non-Final Office Action received in related U.S. Appl. No. 14/579,956 dated Mar. 12, 2015.
Notice of Allowance received in related U.S. Appl. No. 12/647,810 dated Mar. 8, 2013.
Notice of Allowance received in related U.S. Appl. No. 13/755,637 dated Sep. 30, 2014.
Notice of Allowance received in related U.S. Appl. No. 13/925,170 dated Apr. 14, 2014.
Notice of Allowance received in related U.S. Appl. No. 13/926,766 dated Jun. 3, 2014.
Notice of Allowance received in related U.S. Appl. No. 14/449,647 dated Dec. 2, 2014.
Offermans et al., "G alpha 15 and G alpha 16 couple a wide variety of receptors to phospholipase C.," J Bioi Chern (1995) 270(25): 15175-15180.
Parlee et al., "Serum chemerin levels vary with time of day and are modified by obesity and tumor necrosis factor-{alpha}," Endocrinology (2010) 151 (6):2590-2602.
Parolini et al., "The role of chemerin in the colocalization of NK and dendritic cell subsets into inflames tissues," Blood (2007) 555(3):495-499.
Patel et al., "Beta-Arrestin-Mediated Signaling in the Heart", NIH Public Access, Author Manuscript, Circ J., (2008) 72(11): 1725-1729.
Pitcher et al., "G protein-coupled receptor kinases," Annu Rev Biochem (1998) 67:653-692.
Rajagopal, S. et al., "Quantifying Ligand Bias at Seven-Transmembrane Receptors. Molecular Pharmacology", 2011, 80(3):367-377.
Rattan et al., "Protein synthesis, posttranslational modifications, and aging," Ann NY Acad Sci (1992) 663:48-62.
Carpino et al., The 9-fluorenylmethoxycarbonyl amino-protecting group, J Org Chem 1972 37(22):3404-3409.
Non-final Office Action dated Jan. 28, 2016 in related U.S. Appl. No. 14/616,487.
Notice of Allowance dated Aug. 12, 2016 in U.S. Appl. No. 14/616,487.
Notice of Allowance dated Aug. 24, 2016 in U.S. Appl. No. 14/461,081.

Scheme 1

Scheme 2

Scheme 3

SEQUENCE LISTING

<160> NUMBER OF SEQ ID NOS: 5

<210> SEQ ID NO 1
<211> LENGTH: 8
<212> TYPE: PRT

```
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (1)..(1)
<223> OTHER INFORMATION: Sarcosine
<220> FEATURE:
<221> NAME/KEY: MOD_RES
<222> LOCATION: (8)..(8)
<223> OTHER INFORMATION: D-alanine

<400> SEQUENCE: 1

Xaa Arg Val Tyr Ile His Pro Ala
1               5

<210> SEQ ID NO 2
<211> LENGTH: 8
<212> TYPE: PRT
<213> ORGANISM: Artificial Sequence
<220> FEATURE:
<223> OTHER INFORMATION: synthetic sequence
<220> FEATURE:
<221> NAME/KEY: MISC_FEATURE
<222> LOCATION: (1)..(1)
<223> OTHER INFORMATION: R1
<220> FEATURE:
<221> NAME/KEY: MOD_RES
<222> LOCATION: (7)..(7)
<223> OTHER INFORMATION: D-alanine
<220> FEATURE:
<221> NAME/KEY: MISC_FEATURE
<222> LOCATION: (8)..(8)
<223> OTHER INFORMATION: OR4

<400> SEQUENCE: 2

Xaa Val Tyr Ile His Pro Ala Xaa
1               5

<210> SEQ ID NO 3
<211> LENGTH: 7
<212> TYPE: PRT
<213> ORGANISM: Artificial Sequence
<220> FEATURE:
<223> OTHER INFORMATION: SYNTHETIC SEQUENCE
<220> FEATURE:
<221> NAME/KEY: MOD_RES
<222> LOCATION: (6)..(6)
<223> OTHER INFORMATION: D-alanine
<220> FEATURE:
<221> NAME/KEY: MISC_FEATURE
<222> LOCATION: (7)..(7)
<223> OTHER INFORMATION: OR4

<400> SEQUENCE: 3

Val Tyr Ile His Pro Ala Xaa
1               5

<210> SEQ ID NO 4
<211> LENGTH: 10
<212> TYPE: PRT
<213> ORGANISM: Artificial Sequence
<220> FEATURE:
<223> OTHER INFORMATION: synthetic sequence
<220> FEATURE:
<221> NAME/KEY: MISC_FEATURE
<222> LOCATION: (1)..(1)
```

-continued

```
<223> OTHER INFORMATION: Z
<220> FEATURE:
<221> NAME/KEY: MOD_RES
<222> LOCATION: (2)..(2)
<223> OTHER INFORMATION: Sarcosine
<220> FEATURE:
<221> NAME/KEY: MOD_RES
<222> LOCATION: (9)..(9)
<223> OTHER INFORMATION: D-alanine
<220> FEATURE:
<221> NAME/KEY: MISC_FEATURE
<222> LOCATION: (10)..(10)
<223> OTHER INFORMATION: OR4

<400> SEQUENCE: 4

Xaa Xaa Arg Val Tyr Ile His Pro Ala Xaa
1               5                   10

<210> SEQ ID NO 5
<211> LENGTH: 10
<212> TYPE: PRT
<213> ORGANISM: Artificial Sequence
<220> FEATURE:
<223> OTHER INFORMATION: synthetic sequence
<220> FEATURE:
<221> NAME/KEY: MISC_FEATURE
<222> LOCATION: (1)..(1)
<223> OTHER INFORMATION: Z
<220> FEATURE:
<221> NAME/KEY: MOD_RES
<222> LOCATION: (2)..(2)
<223> OTHER INFORMATION: Sarcosine
<220> FEATURE:
<221> NAME/KEY: MOD_RES
<222> LOCATION: (3)..(3)
<223> OTHER INFORMATION: Arginine(NO2)
<220> FEATURE:
<221> NAME/KEY: MOD_RES
<222> LOCATION: (9)..(9)
<223> OTHER INFORMATION: D-Alanine
<220> FEATURE:
<221> NAME/KEY: MISC_FEATURE
<222> LOCATION: (10)..(10)
<223> OTHER INFORMATION: OR4

<400> SEQUENCE: 5

Xaa Xaa Arg Val Tyr Ile His Pro Ala Xaa
1               5                   10
```

SYNTHESIS OF BETA-ARRESTIN EFFECTORS

CROSS-REFERENCE TO RELATED APPLICATIONS

This application claims priority to U.S. Provisional Application No. 62/000,329 filed May 19, 2014, which hereby is incorporated by reference in its entirety.

FIELD

The present disclosure describes synthetic methods of compounds that can act as β-arrestin effectors.

BACKGROUND

U.S. Pat. No. 8,486,885 discloses peptides that act as GPCR agonist of GPCR receptors (e.g., angiotensin II). GPCR agonist causes activation of a heterotrimeric "G protein". Such activation leads to second messenger/downstream signaling (e.g., via diacylglycerol, inositol-triphosphate, calcium, etc.) causing changes in physiological function (e.g., blood pressure and fluid homeostasis). One particular peptide disclosed in U.S. Pat. No. 8,486,885, which is hereby incorporated by reference in its entirety, is referred to therein as "SEQ ID NO. 27", which has the following amino acid sequence: NH2-Sarcosine L-Arginine L-Valine L-Tyrosine L-Isoleucine L-Histidine L-Proline D-Alanine-OH referred to as NH2-Sar-Arg-Val-Tyr-Ile-His-Pro-(D)Ala-OH (SEQ ID NO: 1).

SEQ ID NO. 27 referred to in U.S. Pat. No. 8,486,885 (hereinafter referred as SEQ ID NO: 1) is an agonist of β-arrestin/GRK-mediated signal transduction via AT1 angiotensin receptor. The amino acid sequence, including, but not limited to, formula, variables, derivatives, of the peptide or peptide mimetic of SEQ ID NO. 1, the ability of the compound to effect G protein-mediated signaling or GPCR activity, or the absence of such signaling/activity, methods for preparation of SEQ ID NO: 1, and other related peptides are disclosed in U.S. Pat. No. 8,486,885, the contents of which are incorporated herein by reference in their entirety.

There remains a need in the art for other more cost effective and efficient methods of preparing SEQ ID NO. 1 and related compounds.

SUMMARY

In some embodiments, methods of preparing a compound of Formula 1A

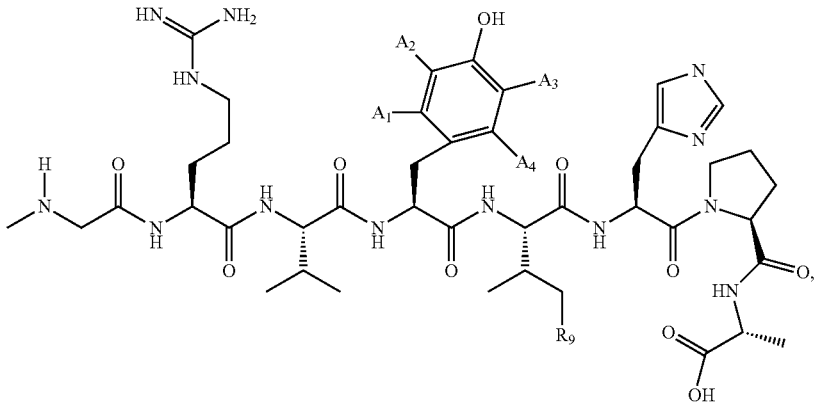

or a pharmaceutically acceptable salt thereof, solvate, or hydrate thereof, are provided. In some embodiments, the method comprises deprotecting a compound of Formula M (M)

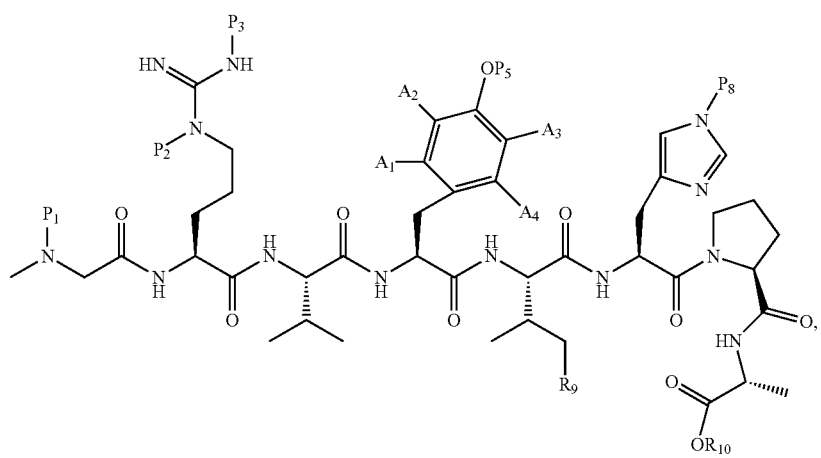

wherein
P₁ is a nitrogen protecting group such as but not limited to, Cbz, Fmoc, Boc, Alloc, TFA;
P₂ is H or a guanidine protecting group such as, but not limited to, NO₂, Boc, Cbz, Pbf;
P₃ is H or a guanidine protecting group such as, but not limited to, NO₂, Boc, Cbz, Pbf;
P₅ is H, tBu, Bom, TBS or other commonly used protecting group for ethers or phenols;
P₈ is H, trityl, tBu, Bom, TBS or other commonly used protecting group for imidazoles;
R₉ is H or methyl;
R₁₀ is H, Me, Et, tBu, Bn, TMS or other protecting group for carboxylic acid;
A₁ is H, OH, F, NO₂, Cl, CH₃, or Br;
A₂ is H, OH, F, NO₂, Cl, CH₃, or Br;
A₃ is H, OH, F, NO₂, Cl, CH₃, or Br; and
A₄ is H, OH, F, NO₂, Cl, CH₃, or Br.

In some embodiments, the deprotecting comprises hydrogenation in a solution of acetic acid. In some embodiments, the deprotecting is performed by hydrogenation with palladium on carbon catalyst. In some embodiments, the compound of Formula 1A is prepared according to the methods described herein, wherein A1, A2, A3, A4, are H and R₉ is methyl.

In some embodiments, the methods comprises preparing a compound of Formula M, the method comprising contacting a compound of Formula K with a compound of Formula C under conditions sufficient to produce a compound of Formula M.

In some embodiments, the methods comprises preparing a compound of Formula K comprising contacting a compound of Formula A with a compound of Formula B under conditions sufficient to produce a compound of Formula K.

In some embodiments, the methods comprises preparing a compound of Formula M, the method comprising contacting a compound of Formula A with a compound of Formula F under conditions sufficient to produce a compound of Formula M.

In some embodiments, the methods comprises preparing a compound of formula F comprising contacting a compound of Formula B and a compound of Formula C under conditions sufficient to produce a compound of Formula F.

In some embodiments, methods of preparing a compound of Formula (1) or SEQ ID NO: 1

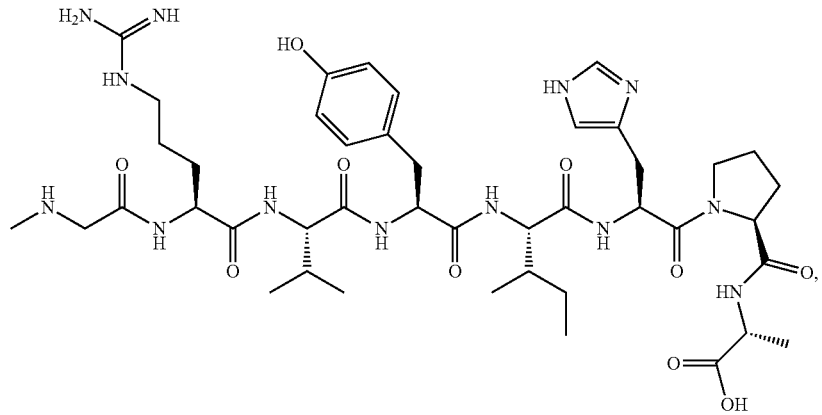

or a pharmaceutically acceptable salt thereof, solvate, or hydrate thereof, the method comprising contacting H-His(HCl)-Pro-(D)-Ala-OR₄ with R₁-Val-Tyr-Ile-OH under conditions sufficient to produce R₁-Val-Tyr-Ile-His-Pro-(D)-Ala-OR₄ (SEQ ID NO: 2); deprotecting R₁-Val-Tyr-Ile-His-Pro-(D)-Ala-OR₄ (SEQ ID NO: 2) to produce H-Val-Tyr-Ile-His-Pro-(D)-Ala-OR₄ (SEQ ID NO: 3); contacting H-Val(acid)-Tyr-Ile-His-Pro-(D)-Ala-OR₄ (SEQ ID NO: 3) with Z-Sar-Arg-OH under conditions sufficient to produce Z-Sar-Arg-Val-Tyr-Ile-His-Pro-(D)-Ala-OR₄ (SEQ ID NO: 4); and deprotecting Z-Sar-Arg-Val-Tyr-Ile-His-Pro-(D)-Ala-OR₄ (SEQ ID NO: 4) to produce

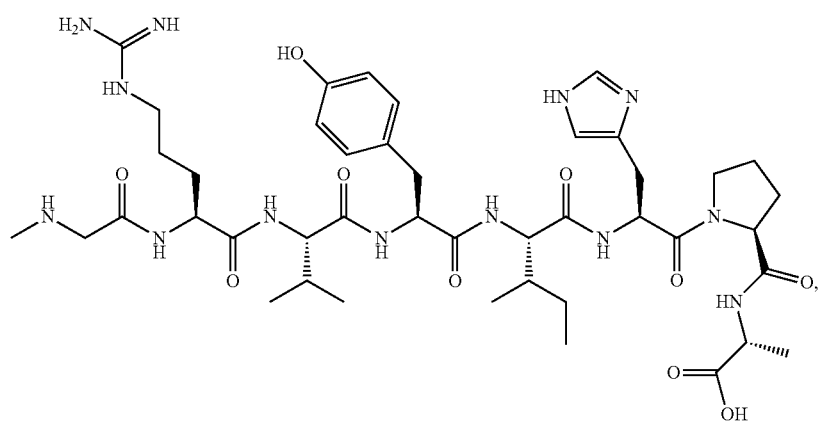

wherein Z is carboxybenzyl; $R_1$ is a nitrogen protecting group; and $R_4$ is H, Me, Et, tert-Bu, Bn, TMS or other carboxylic acid protecting group, In some embodiments, methods of preparing

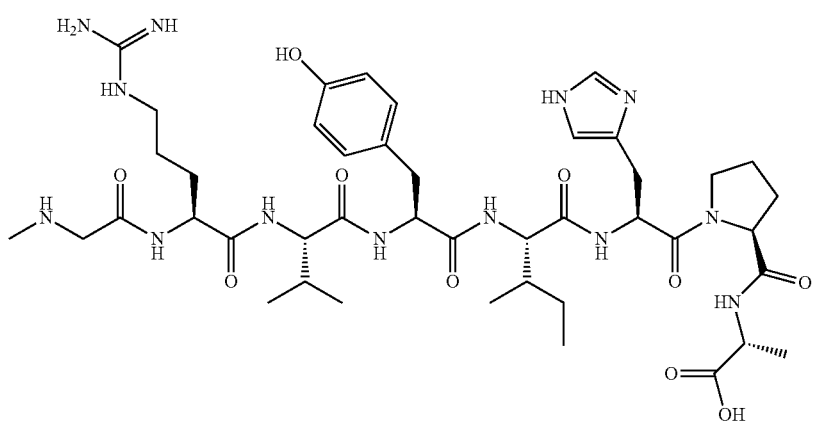

1 or a pharmaceutically acceptable salt thereof, solvate, or hydrate thereof, are provided, the method comprising, a) contacting H-His(HCl)-Pro-(D)-Ala-$OR_4$ with Z-Sar-Arg($NO_2$)-Val-Tyr-Ile-OH under conditions sufficient to produce Z-Sar-Arg($NO_2$)-Val-Tyr-Ile-His-Pro-(D)-Ala-$OR_4$ (SEQ ID NO: 5); and b) hydrogenating Z-Sar-Arg($NO_2$)-Val-Tyr-Ile-His-Pro-(D)-Ala-$OR_4$ (SEQ ID NO: 5) to produce Z-Ser-Arg-OH

4 under conditions sufficient to produce Z-Sar-Arg-Val-Ww-ZZ-His-Pro-(D)-Ala-$OR_4$; and hydrogenating Z-Sar-Arg-Val-Ww-Zz-His-Pro-(D)-Ala-$OR_4$ to produce Sar-Arg-Val-Ww-Zz-His-Pro-(D)-Ala, wherein: Z is carboxybenzyl; $R_1$ is a nitrogen protecting group; $R_4$ is H, Me, Et, tert-Bu, Bn, TMS or other carboxylic acid protecting group, Ww is L-Tyr, 3-hydroxy-L-Tyr, 3-fluoro-L-Tyr, 2,6-difluoro-L-Tyr, 3-nitro-L-Tyr, 3,5-dinitro-L-tyrosine, 3-chloro-L-tyrosine,

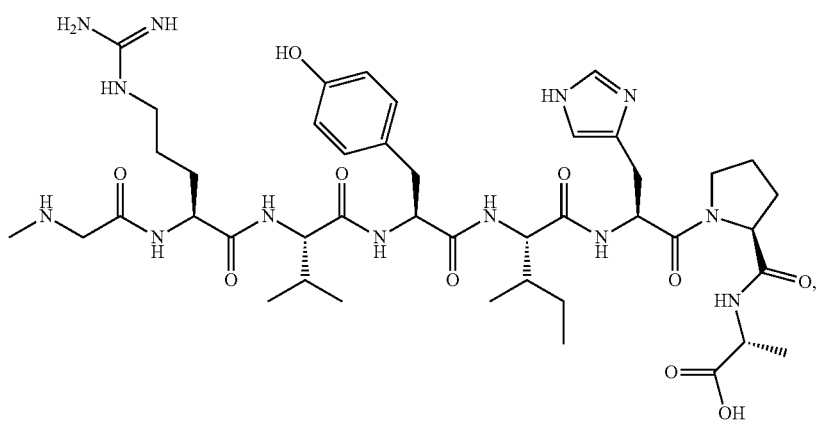

1 wherein Z is carboxybenzyl; and $R_4$ is H, Me, Et, tert-Bu, Bn, TMS or other carboxylic acid protecting group.

In some embodiments, methods of preparing Sar-Arg-Val-Ww-Zz-His-Pro-(D)-Ala are provided. In some embodiments, the method comprises contacting H-His(HCl)-Pro-(D)-Ala-$OR_4$ with $R_1$-Val-Ww-Zz-OH under conditions sufficient to produce $R_1$-Val-Ww-Zz-His-Pro-(D)-Ala-$OR_4$; treating $R_1$-Val-Ww-Zz-His-Pro-(D)-Ala-$OR_4$ with an acid to produce H-Val(HCl)-WW-Zz-His-Pro-(D)-Ala-$OR_4$; contacting H-Val(HCl)-WW-Zz-His-Pro-(D)-Ala-$OR_4$ with 2,6-dimethyl-L-tyrosine, 4-fluorophenyl-L-alanine, 3,5-dibromo-L-tyrosine, or O-allyl-L-tyrosine; and Zz is L-Val or L-Ile.

In some embodiments, methods of preparing a compound of Formula A, B, $B_1$, C, E, F, G, H, J, K, L, and M according to one or more of the schemes described herein are provided.

In some embodiments, methods for preparing a compound of Formula 1, or a pharmaceutically acceptable salt thereof, solvate, or hydrate thereof, are provided, the method comprising deprotecting a compound of formula H:

(H)

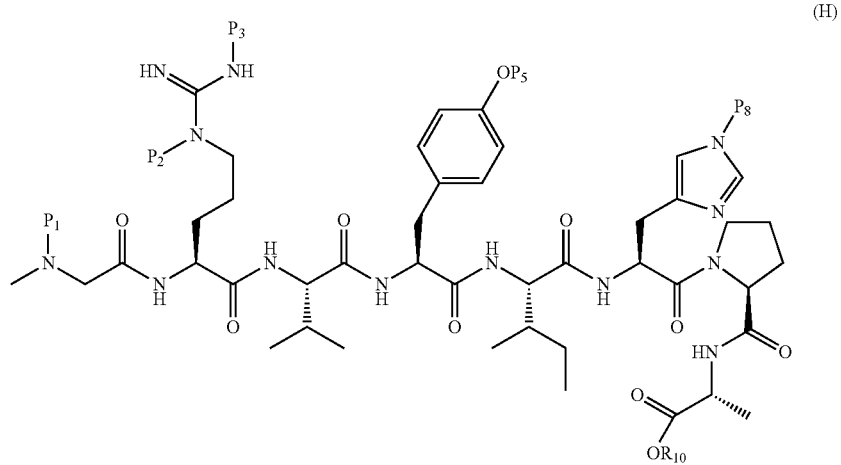

wherein

P₁ is a nitrogen protecting group such as but not limited to, Cbz, Fmoc, Boc, Alloc, TFA;

P₂ is H or a guanidine protecting group such as, but not limited to, NO₂, Boc, Cbz, Pbf;

P₃ is H or a guanidine protecting group such as, but not limited to, NO₂, Boc, Cbz, Pbf;

P₅ is H, tBu, Bom, TBS or other commonly used protecting group for ethers or phenols P₈ is H, trityl, tBu, Bom, TBS or other commonly used protecting group for imidazoles; and R₁₀ is H, Me, Et, tBu, Bn, TMS or other protecting group for carboxylic acid.

In some embodiments, methods for preparing a compound of Formula (1A), or a pharmaceutically acceptable salt thereof, solvate, or hydrate thereof, are provided, the method comprising deprotecting a compound of Formula M:

wherein

P₁ is a nitrogen protecting group such as but not limited to, Cbz, Fmoc, Boc, Alloc, TFA;

P₂ is H or a guanidine group such as, but not limited to, NO₂, Boc, Cbz, Pbf;

P₃ is H or a guanidine group such as, but not limited to, NO₂, Boc, Cbz, Pbf;

P₅ is H, tBu, Bom, TBS or other commonly used protecting group for ethers or phenols;

P₈ is H, trityl, tBu, Bom, TBS or other commonly used protecting group for imidazoles;

R₉ is H or methyl;

R₁₀ is H, Me, Et, tBu, Bn, TMS or other protecting group for carboxylic acid;

A₁ is H, OH, F, NO₂, Cl, CH₃, or Br;

A₂ is H, OH, F, NO₂, Cl, CH₃, or Br;

A₃ is H, OH, F, NO₂, Cl, CH₃, or Br; and

A4 is H, OH, F, NO₂, Cl, CH₃, or Br.

In some embodiments, compounds of Formula A are provided (M)

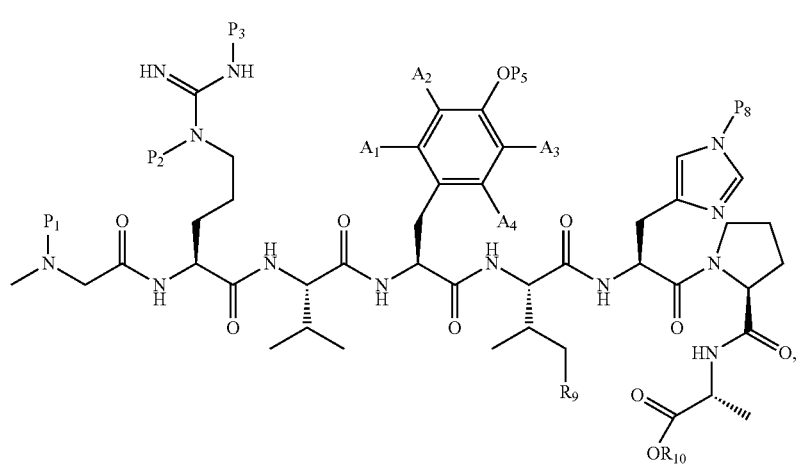

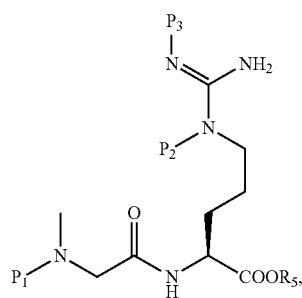

(A)

wherein
P₁ is a nitrogen protecting group such as but not limited to, Cbz, Fmoc, Boc, Alloc, TFA;
P₂ is H or a guanidine protecting group such as, but not limited to, $NO_2$, Boc, Cbz, Pbf;
P₃ is H or a guanidine protecting group such as, but not limited to, $NO_2$, Boc, Cbz, Pbf; and
R₅ is H, Me, Et, tert-Bu, Bn, TMS or a similar carboxylic acid protecting group.

In some embodiments, compounds of Formula B are provided

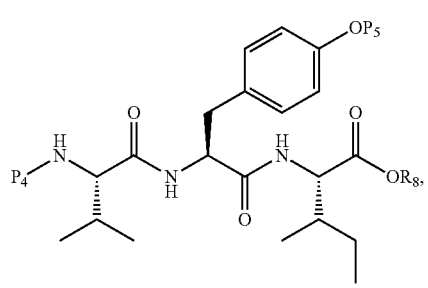

(B)

wherein
P₄ is H, Cbz, Fmoc, Boc, Alloc, TFA or another nitrogen protecting group,
P₅ is tBu, Bom, TBS, allyl, Bn, or other protecting group for ethers or phenols;
R₈ is H, Me, Et, tBu, Bn, TMS or other protecting group for carboxylic acid.

In some embodiments, compounds of Formula B₁ are provided

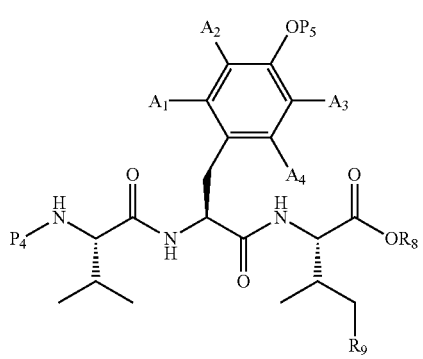

(B₁)

wherein:
P₄ is H, Cbz, Fmoc, Boc, Alloc, TFA or other commonly used nitrogen protecting group;
P₅ is H, tBu, Bom, TBS, allyl or other commonly used protecting group for ethers or phenols;
R₈ is H, Me, Et, tBu, Bn, TMS or other protecting group for carboxylic acid;
R₉ is H or methyl;
A₁ is H, OH, F, $NO_2$, Cl, $CH_3$, or Br;
A₂ is H, OH, F, $NO_2$, Cl, $CH_3$, or Br;
A₃ is H, OH, F, $NO_2$, Cl, $CH_3$, or Br; and
A4 is H, OH, F, $NO_2$, Cl, $CH_3$, or Br.

In some embodiments, compounds of Formula B2, as shown below, are provided.

In some embodiments, compounds of Formula C are provided.

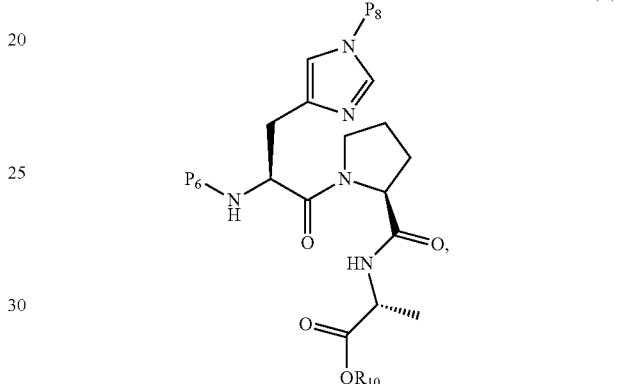

(C)

wherein
P₆ is Cbz, Fmoc, Boc, Alloc, TFA or other commonly used nitrogen protecting group;
P₈ is H, trityl, tBu, Bom, TBS or other commonly used protecting group for imidazoles; and
R₁₀ is H, Me, Et, tBu, Bn, TMS or other protecting group for carboxylic acid.

In some embodiments, compounds of Formula E are provided

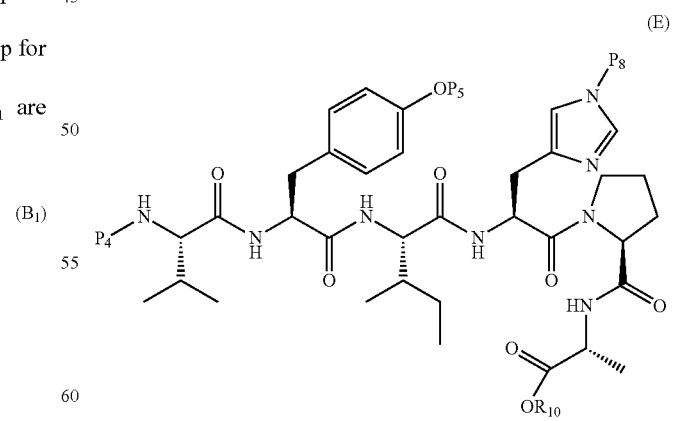

(E)

are provided, wherein
P₄ is H, Cbz, Fmoc, Boc, Alloc, TFA or other commonly used nitrogen protecting group;
P₅ is H, tBu, Bom, TBS, allyl, Bn, or other commonly used protecting group for ethers or phenols;

$P_8$ is H, trityl, tBu, Bom, TBS or other commonly used protecting group for imidazoles $R_{10}$ is H, Me, Et, tBu, Bn, TMS or other protecting group for carboxylic acid.

In some embodiments, compounds of Formula F are provided

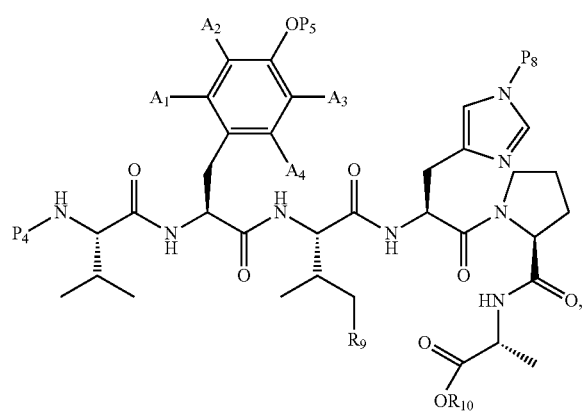

(F)

wherein
$P_4$ is H, Cbz, Fmoc, Boc, Alloc, TFA or other commonly used nitrogen protecting group;
$P_5$ is H, tBu, Bom, TBS, allyl, Bn, or other commonly used protecting group for ethers or phenols
$P_8$ is H, trityl, tBu, Bom, TBS or other commonly used protecting group for imidazoles
$R_9$ is H or methyl;
$R_{10}$ is H, Me, Et, tBu, Bn, TMS or other protecting group for carboxylic acid;
$A_1$ is H, OH, F, $NO_2$, Cl, $CH_3$, or Br;
$A_2$ is H, OH, F, $NO_2$, Cl, $CH_3$, or Br;
$A_3$ is H, OH, F, $NO_2$, Cl, $CH_3$, or Br; and
$A_4$ is H, OH, F, $NO_2$, Cl, $CH_3$, or Br.

In some embodiments, compounds of Formula G are provided (G)

wherein
$P_4$ is H, Cbz, Fmoc, Boc, Alloc, TFA or other commonly used nitrogen protecting group;
$P_8$ is H, trityl, tBu, Bom, TBS or other commonly used protecting group for imidazoles;
$R_9$ is H or methyl; and
$R_{10}$ is H, Me, Et, tBu, Bn, TMS or other protecting group for carboxylic acid, In some embodiments, compounds of Formula H are provided

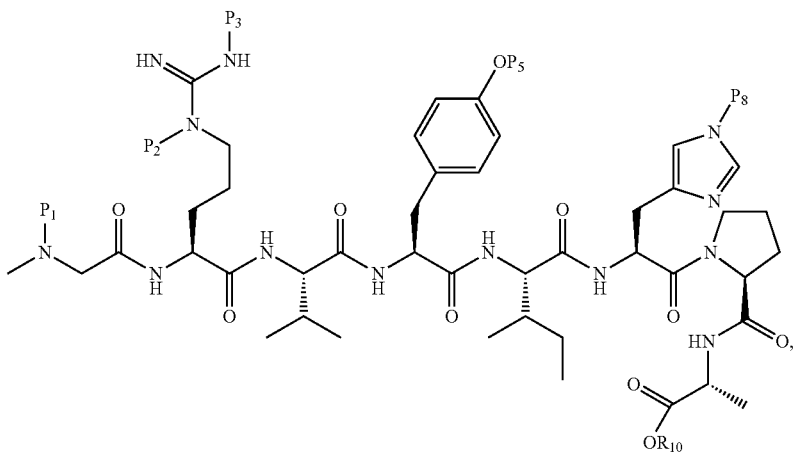

(H)

wherein
$P_1$ is a nitrogen protecting group such as but not limited to, Cbz, Fmoc, Boc, Alloc, TFA;
$P_2$ is H or a guanidine protecting group such as, but not limited to, $NO_2$, Boc, Cbz, Pbf;
$P_3$ is H or a guanidine protecting group such as, but not limited to, $NO_2$, Boc, Cbz, Pbf;
$P_5$ is H, tBu, Bom, TBS, allyl, Bn, or other commonly used protecting group for ethers or phenols
$P_8$ is H, trityl, tBu, Bom, TBS or other commonly used protecting group for imidazoles; and
$R_{10}$ is H, Me, Et, tBu, Bn, TMS or other protecting group for carboxylic acid.

In some embodiments, compounds of Formula J are provided

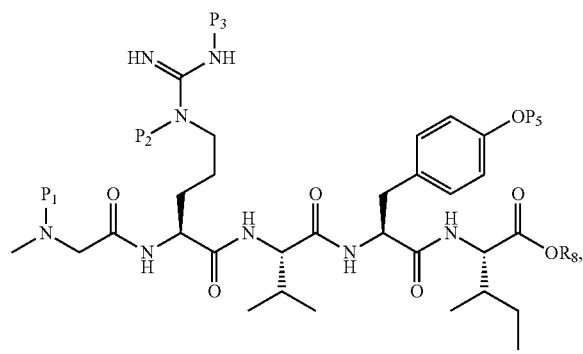

(J)

wherein
$P_1$ is a nitrogen protecting group such as but not limited to, Cbz, Fmoc, Boc, Alloc, TFA;
$P_2$ is H or a guanidine protecting group such as, but not limited to, $NO_2$, Boc, Cbz, Pbf;
$P_3$ is H or a guanidine protecting group such as, but not limited to, $NO_2$, Boc, Cbz, Pbf;
$P_5$ is H, tBu, Bom, TBS, allyl, Bn, or other commonly used protecting group for ethers or phenols; and
$R_8$ is H, Me, Et, tBu, Bn, TMS or other protecting group for carboxylic acid.

In some embodiments, compounds of Formula K are provided

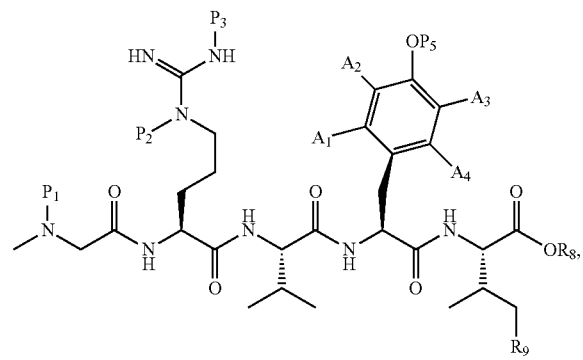

(K)

wherein
$P_1$ is a nitrogen protecting group such as but not limited to, Cbz, Fmoc, Boc, Alloc, TFA;
$P_2$ is H or a guanidine protecting group such as, but not limited to, $NO_2$, Boc, Cbz, Pbf;
$P_3$ is H or a guanidine protecting group such as, but not limited to, $NO_2$, Boc, Cbz, Pbf;
$P_5$ is H, tBu, Bom, TBS, allyl, Bn, or other commonly used protecting group for ethers or phenols; and
$R_8$ is H, Me, Et, tBu, Bn, TMS or other protecting group for carboxylic acid;
$R_9$ is H or methyl;
$A_1$ is H, OH, F, $NO_2$, Cl, $CH_3$, or Br;
$A_2$ is H, OH, F, $NO_2$, Cl, $CH_3$, or Br;
$A_3$ is H, OH, F, $NO_2$, Cl, $CH_3$, or Br; and
$A_4$ is H, OH, F, $NO_2$, Cl, $CH_3$, or Br.

In some embodiments, compounds of Formula L are provided

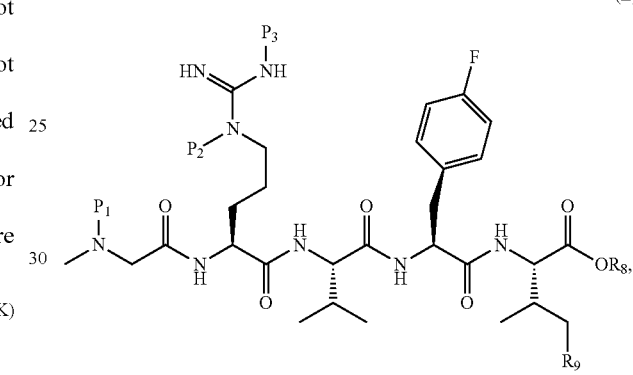

(L)

wherein
$P_1$ is a nitrogen protecting group such as but not limited to, Cbz, Fmoc, Boc, Alloc, TFA;
$P_2$ is H or a guanidine protecting group such as, but not limited to, $NO_2$, Boc, Cbz, Pbf;
$P_3$ is H or a guanidine protecting group such as, but not limited to, $NO_2$, Boc, Cbz, Pbf;
$R_8$ is H, Me, Et, tBu, Bn, TMS or other protecting group for carboxylic acid; and
$R_9$ is H or methyl.

In some embodiments, compounds of Formula M are provided

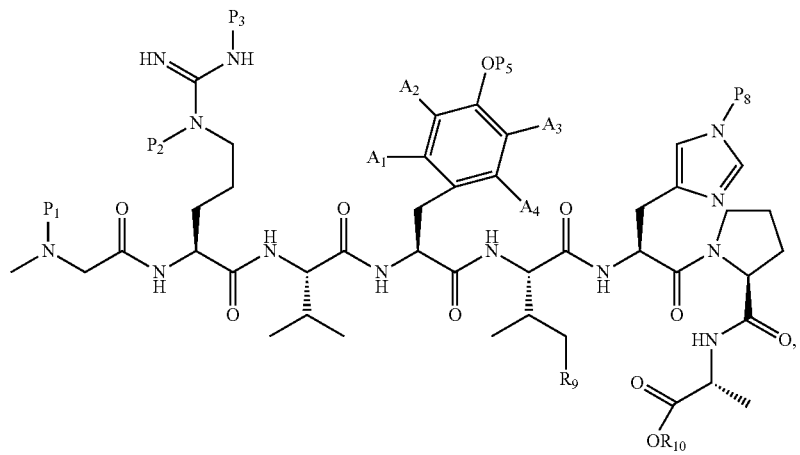

(M)

wherein
P₁ is a nitrogen protecting group such as but not limited to, Cbz, Fmoc, Boc, Alloc, TFA;
P₂ is H or a guanidine group such as, but not limited to, NO₂, Boc, Cbz, Pbf;
P₃ is H or a guanidine group such as, but not limited to, NO₂, Boc, Cbz, Pbf;
P₅ is H, tBu, Bom, TBS, allyl, Bn, or other commonly used protecting group for ethers or phenols;
P₈ is H, trityl, tBu, Bom, TBS or other commonly used protecting group for imidazoles;

R₉ is H or methyl;
R₁₀ is H, Me, Et, tBu, Bn, TMS or other protecting group for carboxylic acid;
A₁ is H, OH, F, NO₂, Cl, CH₃, or Br;
A₂ is H, OH, F, NO₂, Cl, CH₃, or Br;
A₃ is H, OH, F, NO₂, Cl, CH₃, or Br; and
A4 is H, OH, F, NO₂, Cl, CH₃, or Br.

In some embodiments, compounds of Formula 2, 3, 4, 5, 6, 7, 8, 9, and 10 are provided:

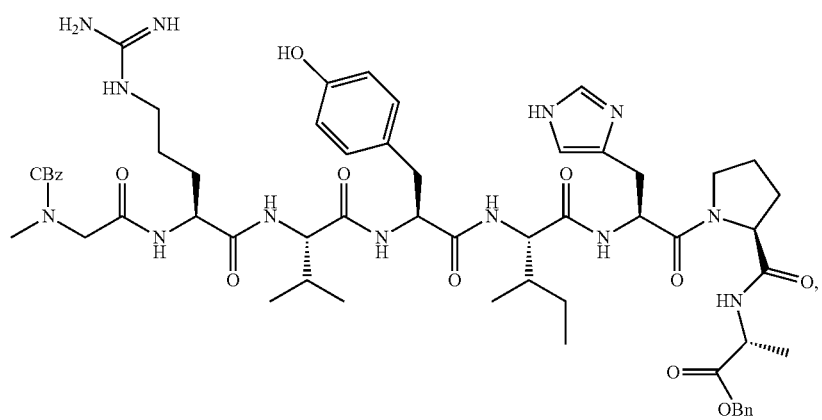

2

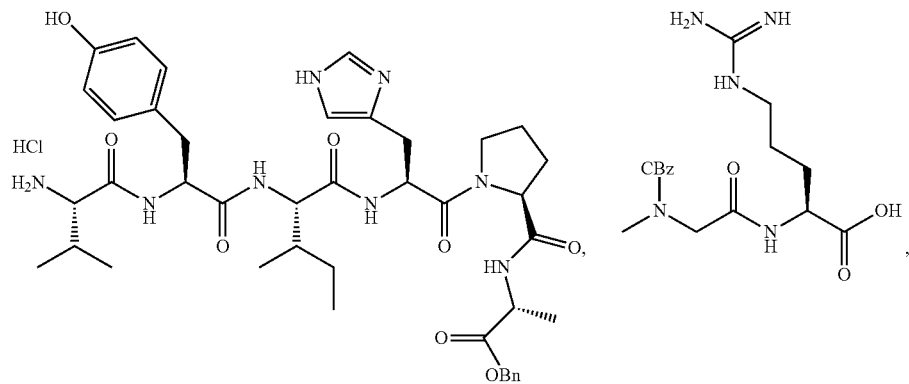

3

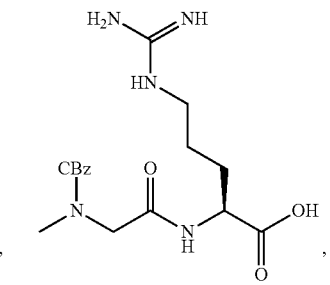

4

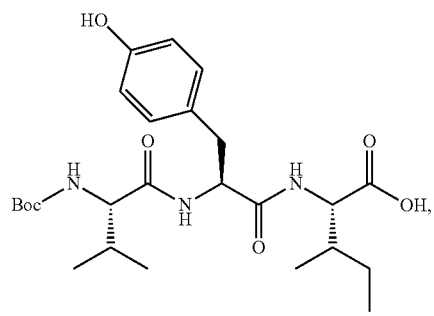

5

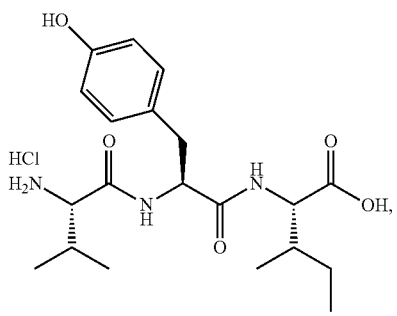

6

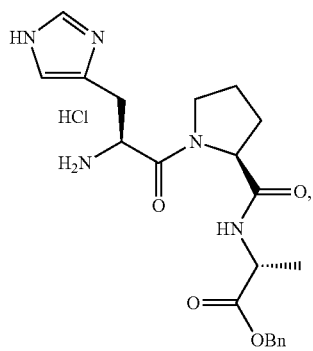

7

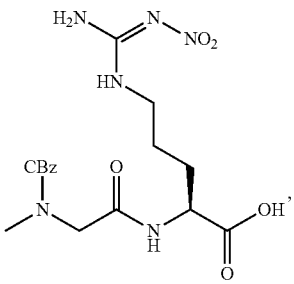

8

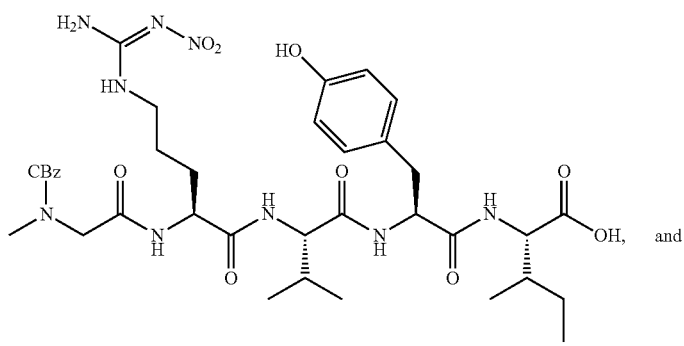

9 and

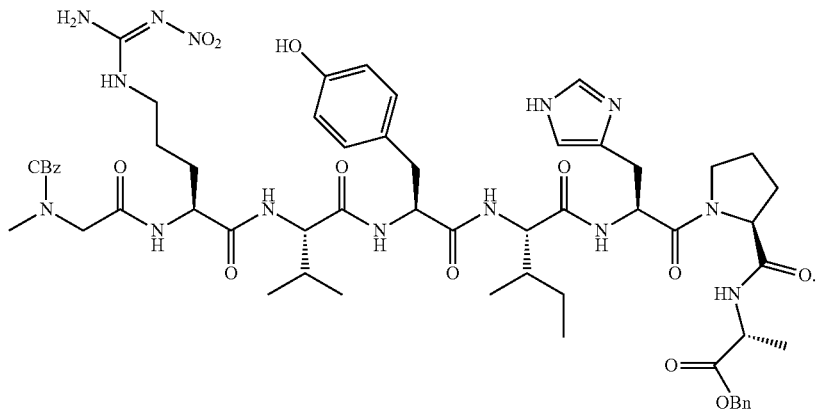

10

In some embodiments, any compound is described herein is provided. In some embodiments, the compound is a not a compound of Formula 1 or Formula 1A.

In some embodiments, a solution comprising a compound described herein is provided. In some embodiments, the solution does not comprise a compound of Formula 1 or Formula 1A.

In some embodiments an activated compound of a compound described herein is provided. In some embodiments, the activated compound is not a compound of Formula 1 or 1A. In some embodiments a solution comprising the activated compound is provided.

DETAILED DESCRIPTION

Figure 1:
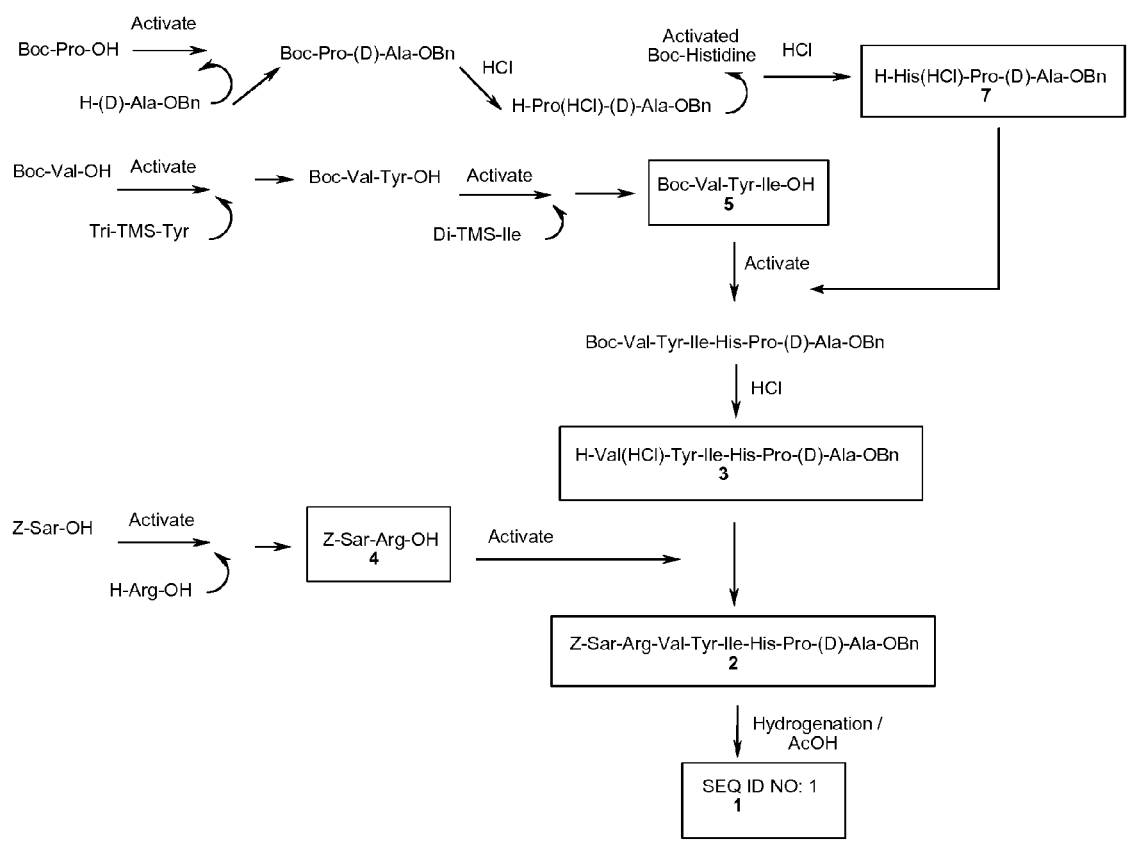
FIG. 1 depicts an exemplary scheme, Scheme 1, a process for preparing SEQ ID NO: 1.

Unless otherwise defined, all technical and scientific terms used herein have the same meaning as commonly understood by one of ordinary skill in the art. Although methods and materials similar or equivalent to those described herein can be used in the practice or testing, suitable methods and materials are described herein. All publications, patent applications, patents, and other references mentioned herein are incorporated by reference in their entirety. In the case of conflict, the present specification, including definitions, will control. In addition, the materials, methods, and examples are illustrative only and not intended to be limiting. Other features and advantages of the embodiments disclosed herein will be apparent from the present detailed description and claims.

The term "salt" or "salts" may refer to any acid addition salts, including addition salts of free acids or addition salts of free bases. All of these salts (or other similar salts) may be prepared by conventional means. All such salts are acceptable provided that they are non-toxic and do not substantially interfere with the desired pharmacological activity.

The term "pharmaceutically acceptable" or "therapeutically acceptable" refers to molecular entities and compositions that are physiologically tolerable and preferably do not typically produce an allergic or similar untoward reaction, such as gastric upset, dizziness and the like, when administered to a human. Preferably, as used herein, the term "pharmaceutically acceptable" means approved by a regulatory agency of the Federal or a State government or listed in the U.S. Pharmacopeia or other generally recognized pharmacopeia (e.g., Remington's Pharmaceutical Sciences, Mack Publishing Co. (A. R. Gennaro edit. 1985)) for use in animals, and more particularly in humans.

The term "about" or "approximately" means plus or minus 5%.

As used herein and in the appended claims, the singular forms "a", "an", and "the" include plural reference unless the context clearly dictates otherwise.

The term "CBz-Sar" refers to a sarcosine residue protected by a carboxybenzyl group. CBz-Sar can also be represented as "Z-Sar."

The term "CBz" or "Cbz" refers to carboxybenzyl group. A carboxybenzyl group can also be referred to, or shown, as "OBn" in a formula of a compound.

Due to the vast importance of peptides in biological processes, there is a need for synthetic peptides to be used in a wide variety of applications. Development of solid phase peptide synthesis methodology has increased the availability of peptide compounds. However, the classical solution phase approach still retains its usefulness, especially when performed on a large scale. Some of the approved peptide pharmaceuticals currently produced by chemical synthesis in solution include oxytocin, desmopressin, leuprolide, goserelin, and octreotide.

Embodiments disclosed herein provide a solution phase synthesis of SEQ ID NO: 1 and other related compounds. The octapeptide sequence can be prepared according to several routes. In addition to novel and non-obvious tactical approaches such as the use of O, N-bis/tri-TMS-amino acids and activating agents like pentafluorophenyl ester, the synthesis had the advantage of using only minimum orthogonal protection of side chain functional groups in arginine, tyrosine, and histidine to achieve maximum atom and step economy, which also led to, in some embodiments, no column chromatography in preparing a compound, such as SEQ ID NO: 1.

SEQ ID NO: 1, which can also be referred to as Formula 1, can be represented by the following formula NH2-Sar-Arg-Val-Tyr-Ile-His-Pro-(D)Ala-OH. SEQ ID NO: 1 can also be represented by the formula of:

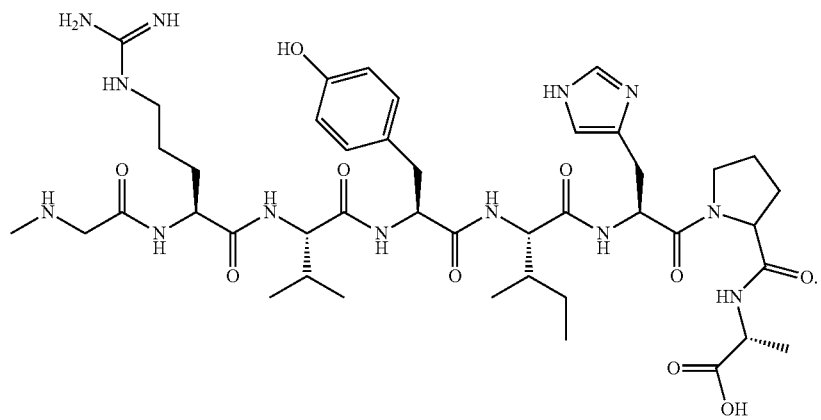

As used herein the terms "comprise," "have," and "include" and their conjugates, as used herein, mean "including but not limited to." While various compositions, methods, and devices are described in terms of "comprising" various components or steps (interpreted as meaning "including, but not limited to"), the compositions, methods, and devices can also "consist essentially of" or "consist of" the various components and steps.

Methods described herein provide for the preparation of SEQ ID NO: 1 (Formula 1) and/or the preparation of Formula 1A. The compounds can be prepared according to schemes and methods described herein, including, but not limited to, the schemes described in the Examples. Additionally, the methods described herein provide methods of preparing the intermediates.

In some embodiments, methods of preparing intermediates are also provided. In some embodiments, the methods comprise contacting

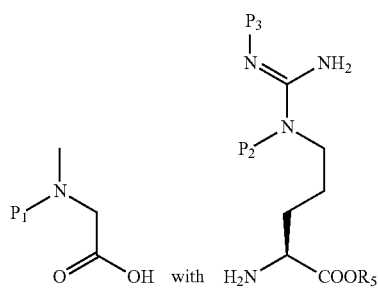

under conditions sufficient to produce a compound of Formula A,

21

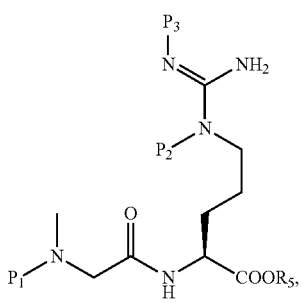

wherein

P₁ is a nitrogen protecting group such as but not limited to, Cbz, Fmoc, Boc, Alloc, TFA;

P₂ is H or a guanidine protecting group such as, but not limited to, NO₂, Boc, Cbz, Pbf;

P₃ is H or a guanidine protecting group such as, but not limited to, NO₂, Boc, Cbz, Pbf; and R₅ is H, Me, Et, tert-Bu, Bn, TMS or a similar carboxylic acid protecting group.

Methods of preparing a compound of Formula B are also provided:

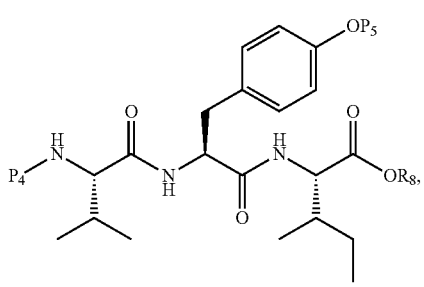

Formula B wherein

P₄ is H, Cbz, Fmoc, Boc, Alloc, TFA or another nitrogen protecting group,

P₅ is tBu, Bom, TBS, allyl, Bn, or other protecting group for ethers or phenols;

R₈ is H, Me, Et, tBu, Bn, TMS or other protecting group for carboxylic acid

In some embodiments, a compound of Formula B is prepared according to the following scheme:

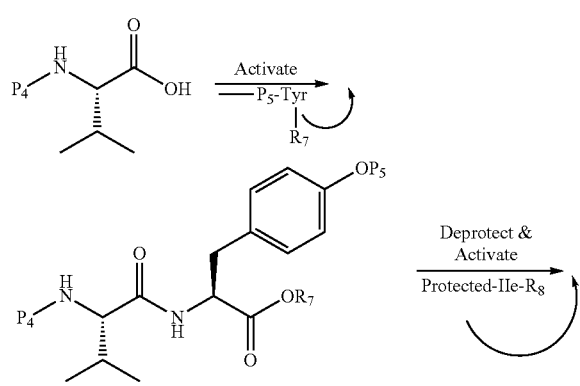

22

-continued

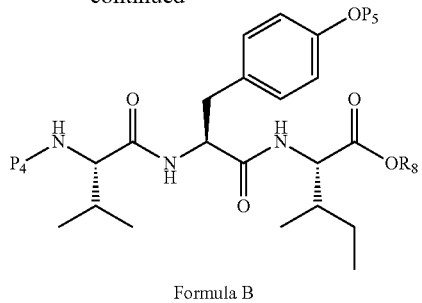

Formula B wherein:

P₄ is H, Cbz, Fmoc, Boc, Alloc, TFA or another nitrogen protecting group,

P₅ is tBu, Bom, TMS, TBS, allyl, Bn, or other protecting group for ethers or phenols;

R₇ is H, Me, Et, tBu, Bn, TMS or other protecting group for carboxylic acid; and R₈ is H, Me, Et, tBu, Bn, TMS or other protecting group for carboxylic acid. Examples of activating agents include, but are not limited to, pentafluorophenyl trifluoroacetate, pentafluorophenyl ester, carbodiimide reagents, chloroformates or N-acylbenzotriazoles. One of skill in the art can choose the appropriate activating agent based upon the present disclosure.

Other examples of compounds that can be made according to similar schemes as shown for Formula B include, but are not limited to, compound of the formula:

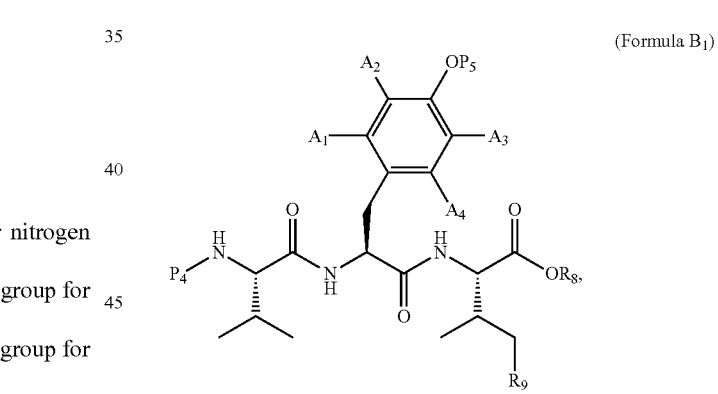

(Formula B₁)

wherein:

P₄ is H, Cbz, Fmoc, Boc, Alloc, TFA or other commonly used nitrogen protecting group;

P₅ is H, tBu, Bom, TBS, allyl or other commonly used protecting group for ethers or phenols;

R₈ is H, Me, Et, tBu, Bn, TMS or other protecting group for carboxylic acid;

R₉ is H or methyl;

A₁ is H, OH, F, NO₂, Cl, CH₃, or Br;

A₂ is H, OH, F, NO₂, Cl, CH₃, or Br;

A₃ is H, OH, F, NO₂, Cl, CH₃, or Br; and

A4 is H, OH, F, NO₂, Cl, CH₃, or Br.

Another non-limiting example of a compound of Formula B that can be prepared by modifying the scheme above, includes, but is not limited to, a compound of formula:

(Formula B₂)

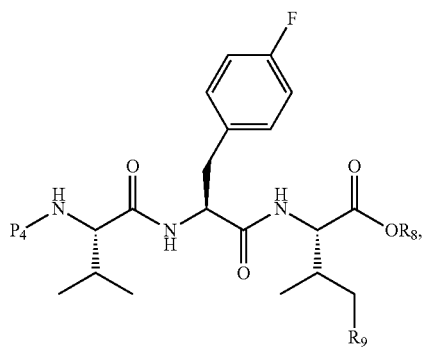

wherein:
P₄ is H, Cbz, Fmoc, Boc, Alloc, TFA or other commonly used nitrogen protecting group;
R₈ is H, Me, Et, tBu, Bn, TMS; and
R₉ is H or methyl.

In some embodiments, methods are provided for preparing a compound of Formula C:

(Formula C)

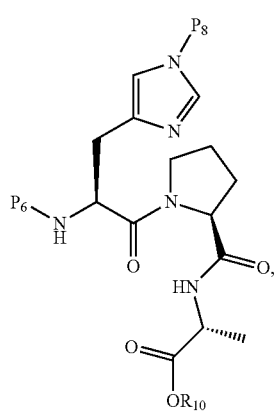

are provided, wherein
P₆ is Cbz, Fmoc, Boc, Alloc, TFA or other commonly used nitrogen protecting group;
P₈ is H, trityl, tBu, Bom, TBS or other commonly used protecting group for imidazoles; and
R₁₀ is H, Me, Et, tBu, Bn, TMS or other protecting group for carboxylic acid.

In some embodiments, a compound of Formula C is prepared according to the following scheme comprising one or more of the steps shown below:

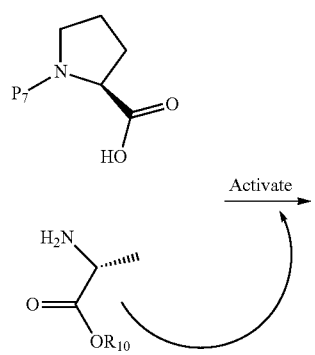

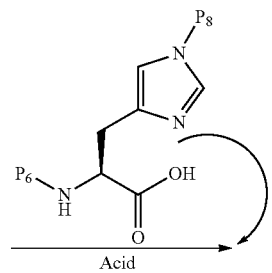

-continued

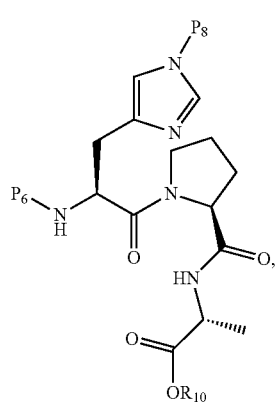

Formula C wherein:
P₇ is Cbz, Fmoc, Boc, Alloc, TFA or other commonly used nitrogen protecting group;
P₆ is Cbz, Fmoc, Boc, Alloc, TFA or other commonly used nitrogen protecting group;
P₈ is H, trityl, tBu, Bom, TBS or other commonly used protecting group for imidazoles; and
R₁₀ is H, Me, Et, tBu, Bn, TMS or other protecting group for carboxylic acid. A compound of Formula C can also be treated with an acid (e.g., HCl) to form a compound of Formula C complexed with the acid. An example of such a compound include, but is not limited to a compound of Formula 7 as shown in Schemes 1, 2, and 3.

In some embodiments, methods of preparing a compound of Formula E (E)

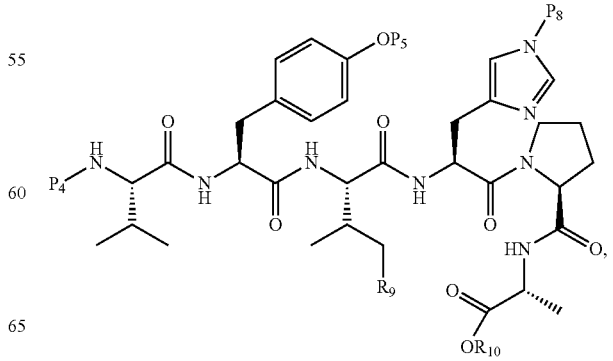

are provided, wherein

P$_4$ is H, Cbz, Fmoc, Boc, Alloc, TFA or other commonly used nitrogen protecting group;

P$_5$ is H, tBu, Bom, TBS, allyl, Bn, or other commonly used protecting group for ethers or phenols;

P$_8$ is H, trityl, tBu, Bom, TBS or other commonly used protecting group for imidazoles;

R$_{10}$ is H, Me, Et, tBu, Bn, TMS or other protecting group for carboxylic acid, wherein the method comprises contacting a compound having a compound of Formula B with a compound having a compound of Formula C under conditions sufficient to produce a compound of Formula E. In some embodiments, a compound of Formula E is produced according to the following scheme:

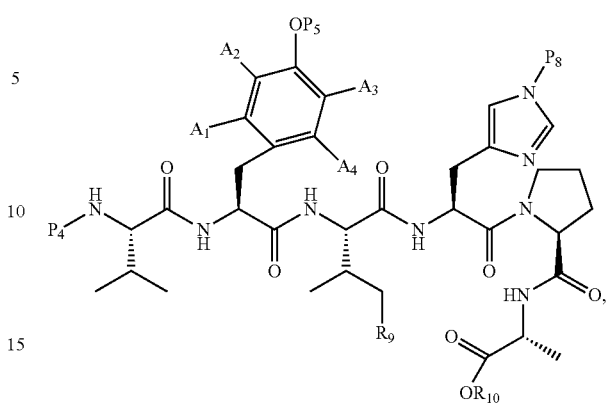

(F)

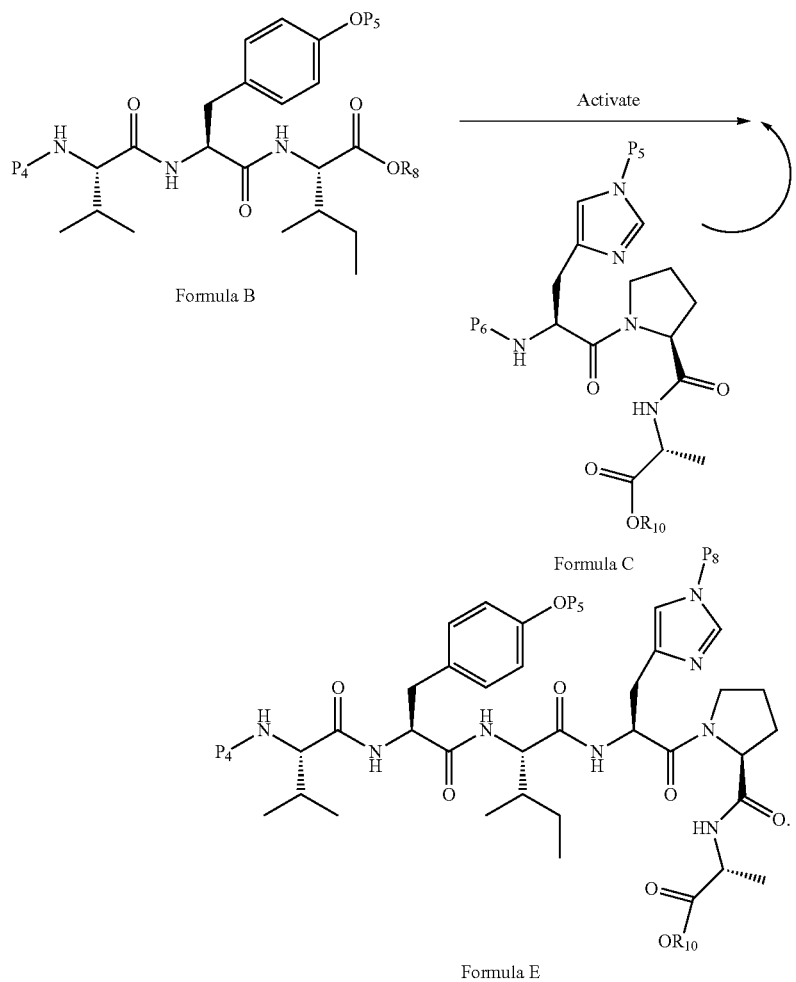

The conditions for preparing a compound of Formula E are described herein and in the examples. For example, a compound of Formula B can be activated using pentafluorophenyl trifluoroacetate, carbodiimide reagents, or N-acylbenzotriazoles. An pentafluorophenyl ester can be formed using pentafluorophenyl trifluoroacetate. One of skill in the art can select the suitable activation agent for the appropriate scheme and compound produced according to the present disclosure and by reference to the specific examples contained herein.

In some embodiments, methods of preparing a compound of Formula F are provided, wherein P$_4$ is H, Cbz, Fmoc, Boc, Alloc, TFA or other commonly used nitrogen protecting group;

P$_5$ is H, tBu, Bom, TBS, allyl, Bn, or other commonly used protecting group for ethers or phenols;

P$_8$ is H, trityl, tBu, Bom, TBS or other commonly used protecting group for imidazoles;

R$_9$ is H or methyl;

R$_{10}$ is H, Me, Et, tBu, Bn, TMS or other protecting group for carboxylic acid;

A₁ is H, OH, F, NO₂, Cl, CH₃, or Br;
A₂ is H, OH, F, NO₂, Cl, CH₃, or Br;
A₃ is H, OH, F, NO₂, Cl, CH₃, or Br; and
A₄ is H, OH, F, NO₂, Cl, CH₃, or Br,
wherein the method comprises contacting a compound of Formula B₁ with a compound of Formula C under conditions sufficient to produce a compound of Formula F. In some embodiments, a compound of Formula F is produced according to the following scheme:

wherein the variables are as defined herein for the specific compounds. The conditions for preparing a compound of Formula F are described herein and, for example, in the examples. One of skill in the art can select the suitable activation agent for the appropriate scheme and compound produced according to the present disclosure and by reference to the specific examples contained herein.

In some embodiments, methods of preparing a compound of Formula G

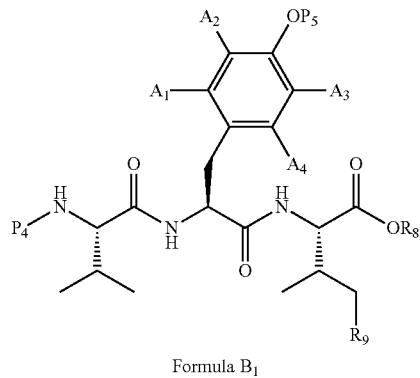

Formula B₁

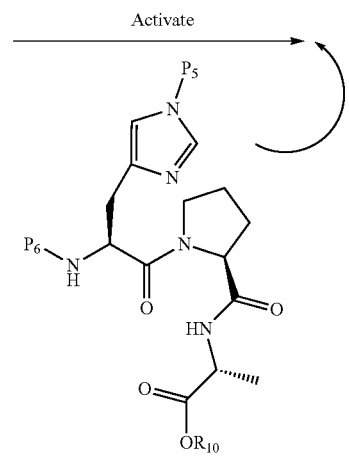

Formula C

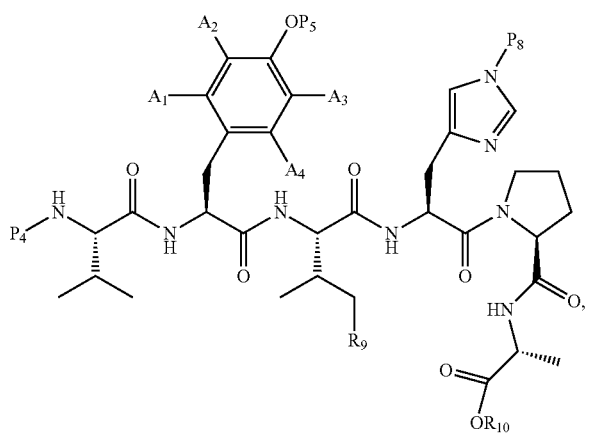

Formula F (G)

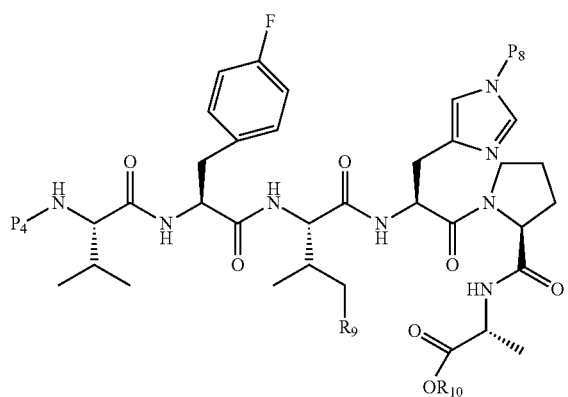

is provided, wherein

P₄ is H, Cbz, Fmoc, Boc, Alloc, TFA or other commonly used nitrogen protecting group;

P₈ is H, trityl, tBu, Bom, TBS or other commonly used protecting group for imidazoles;

R₉ is H or methyl; and

R₁₀ is H, Me, Et, tBu, Bn, TMS or other protecting group for carboxylic acid, wherein the method comprises preparing a compound according contacting a compound of Formula B₂ with a compound of Formula C under conditions sufficient to produce a compound of Formula G. In some embodiments, a compound of Formula F is produced according to the following scheme:

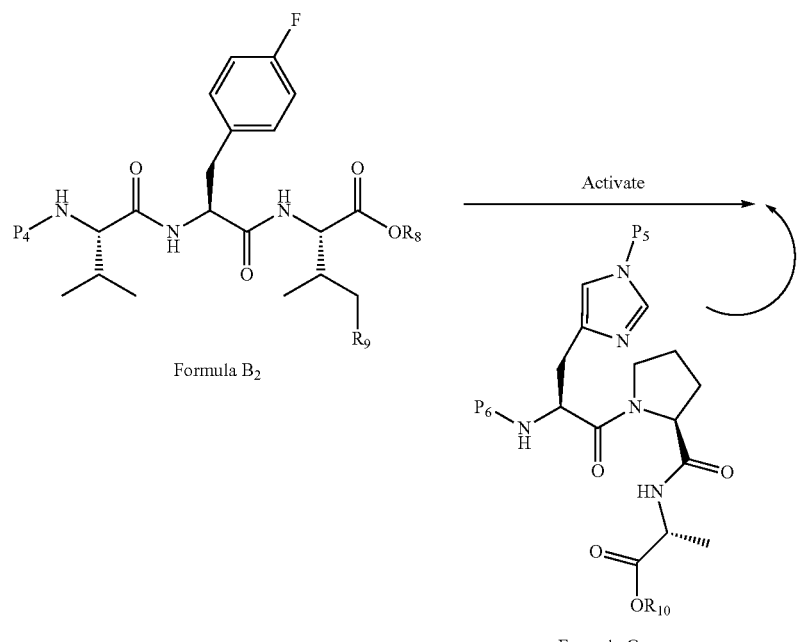

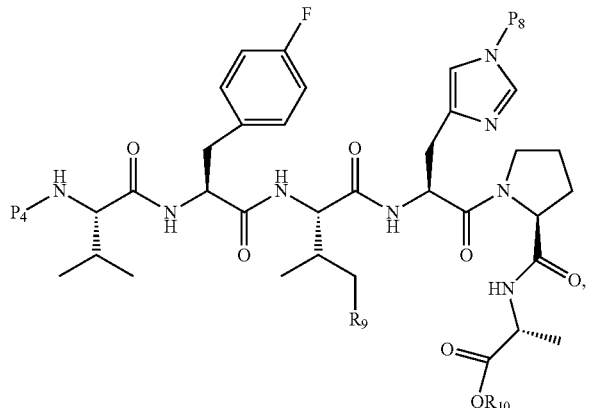

Formula G wherein the variables are as defined herein for the specific compounds. The conditions for preparing a compound of Formula G are described herein and, for example, in the examples. One of skill in the art can select the suitable activation agent for the appropriate scheme and compound produced according to the present disclosure and by reference to the specific examples contained herein.

In some embodiments, methods of preparing a compound of Formula H

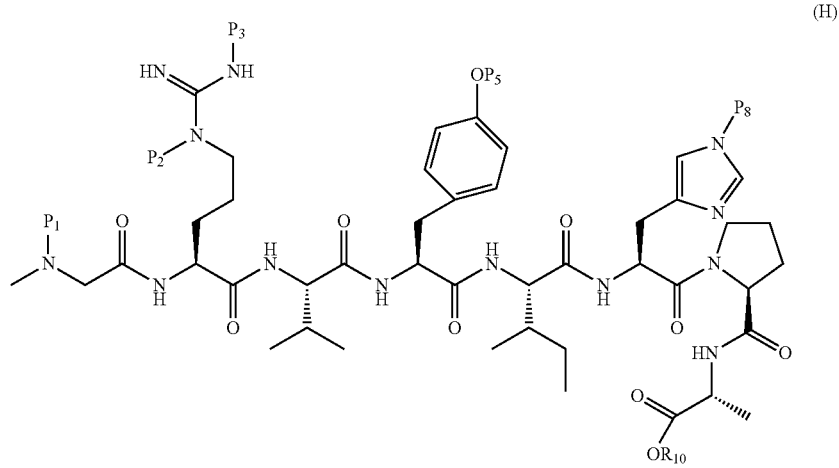

(H)

are provided, wherein $P_1$ is a nitrogen protecting group such as but not limited to, Cbz, Fmoc, Boc, Alloc, TFA;

$P_2$ is H or a guanidine protecting group such as, but not limited to, $NO_2$, Boc, Cbz, Pbf;

$P_3$ is H or a guanidine protecting group such as, but not limited to, $NO_2$, Boc, Cbz, Pbf;

$P_5$ is H, tBu, Bom, TBS, allyl, Bn, or other commonly used protecting group for ethers or phenols $P_8$ is H, trityl, tBu, Bom, TBS or other commonly used protecting group for imidazoles; and $R_{10}$ is H, Me, Et, tBu, Bn, TMS or other protecting group for carboxylic acid.

In some embodiments, the method comprises contacting a compound of Formula E with a compound of Formula A under conditions sufficient to produce a compound of Formula H. In some embodiments, a compound of Formula H is produced according to the following scheme:

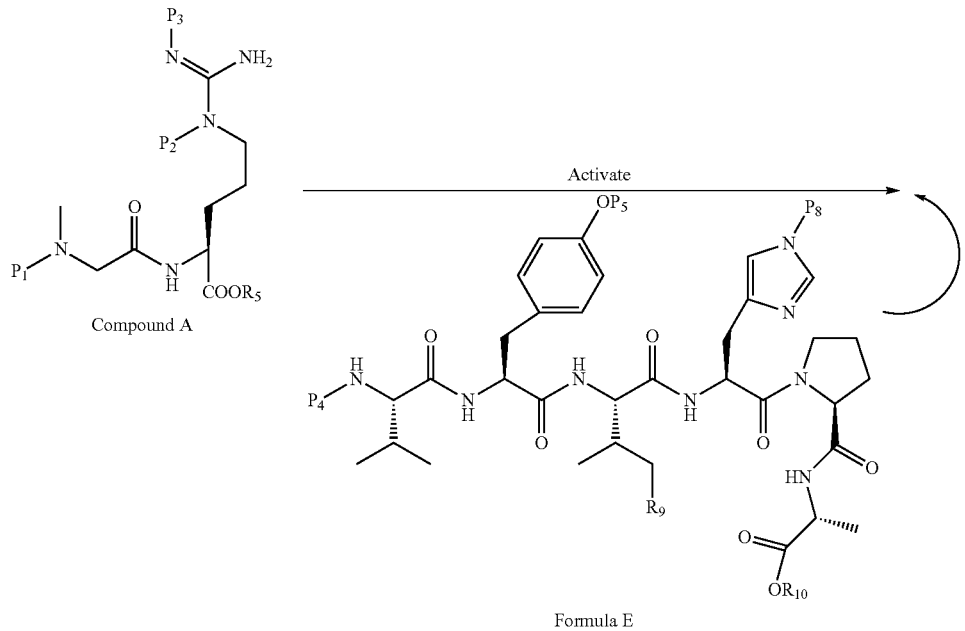

-continued

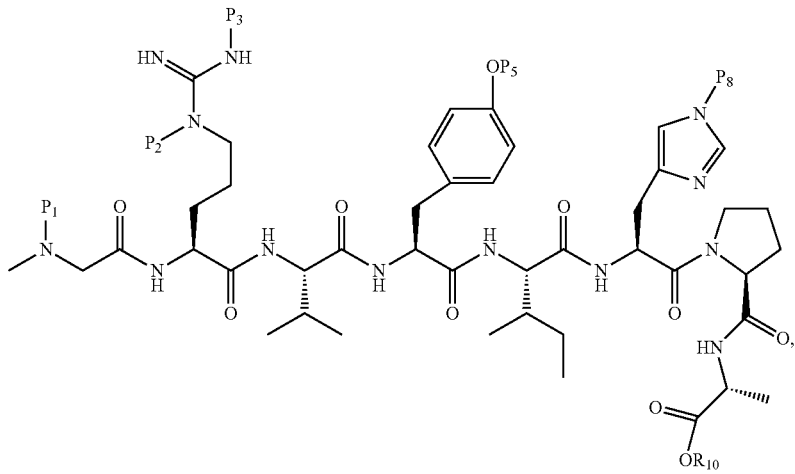

Formula H wherein the variables are as defined herein for the specific compounds. The conditions for preparing a compound of Formula H are described herein and, for example, in the examples. One of skill in the art can select the suitable activation agent for the appropriate scheme and compound produced according to the present disclosure and by reference to the specific examples contained herein. In some embodiments, a compound of Formula H is deprotected, (e.g. hydrogenated) to produce a compound of Formula 1. The hydrogenation can be performed, for example, in a solution of acetic acid (AcOH) as shown in some of the embodiments disclosed herein.

In some embodiments, methods of preparing a compound of Formula J (J)

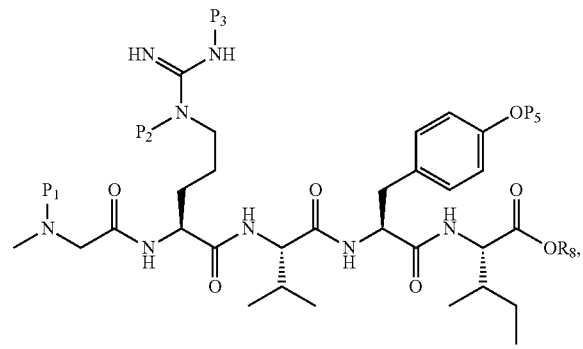

are provided, wherein $P_1$ is a nitrogen protecting group such as but not limited to, Cbz, Fmoc, Boc, Alloc, TFA;

$P_2$ is H or a guanidine protecting group such as, but not limited to, $NO_2$, Boc, Cbz, Pbf;

$P_3$ is H or a guanidine protecting group such as, but not limited to, $NO_2$, Boc, Cbz, Pbf;

$P_5$ is H, tBu, Bom, TBS, allyl, Bn, or other commonly used protecting group for ethers or phenols; and $R_8$ is H, Me, Et, tBu, Bn, TMS or other protecting group for carboxylic acid.

In some embodiments, a compound of Formula J is prepared by contacting a compound of Formula A with a compound of Formula B under conditions sufficient to produce a compound of Formula J. In some embodiments, a compound of Formula J is produced according to the following scheme:

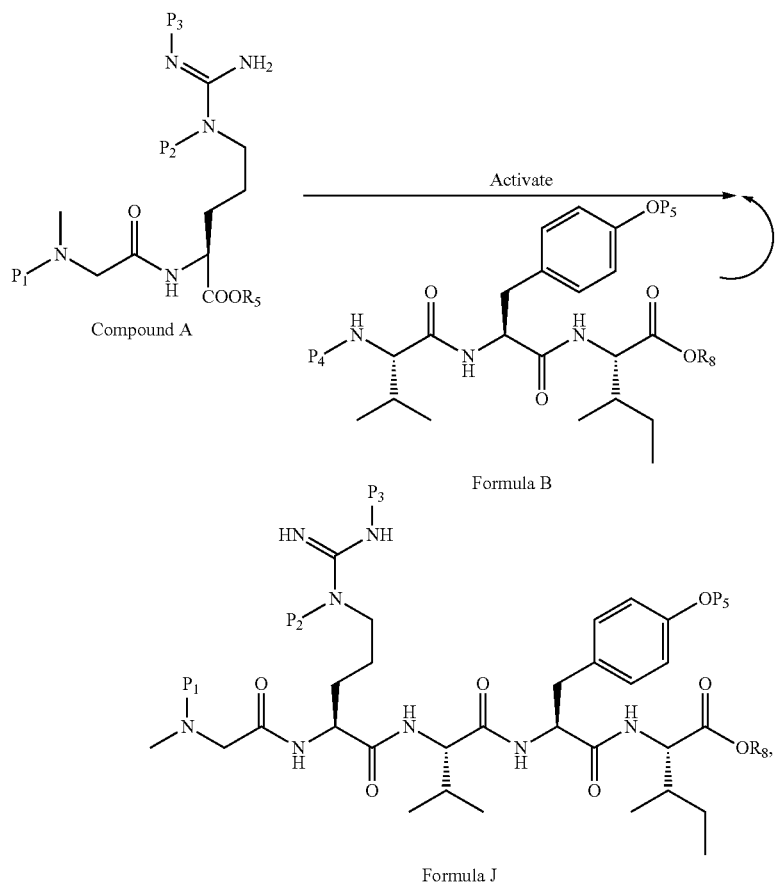

Formula B

Formula J wherein the variables are as defined herein for the specific compounds. The conditions for preparing a compound of Formula J are described herein and, for example, in the examples. One of skill in the art can select the suitable activation agent for the appropriate scheme and compound produced according to the present disclosure and by reference to the specific examples contained herein.

In some embodiments, a method of preparing a compound of Formula H comprises contacting a compound of Formula C with a compound of Formula J under conditions sufficient to produce a compound of Formula H. In some embodiments, a compound of Formula H is produced according to the following scheme:

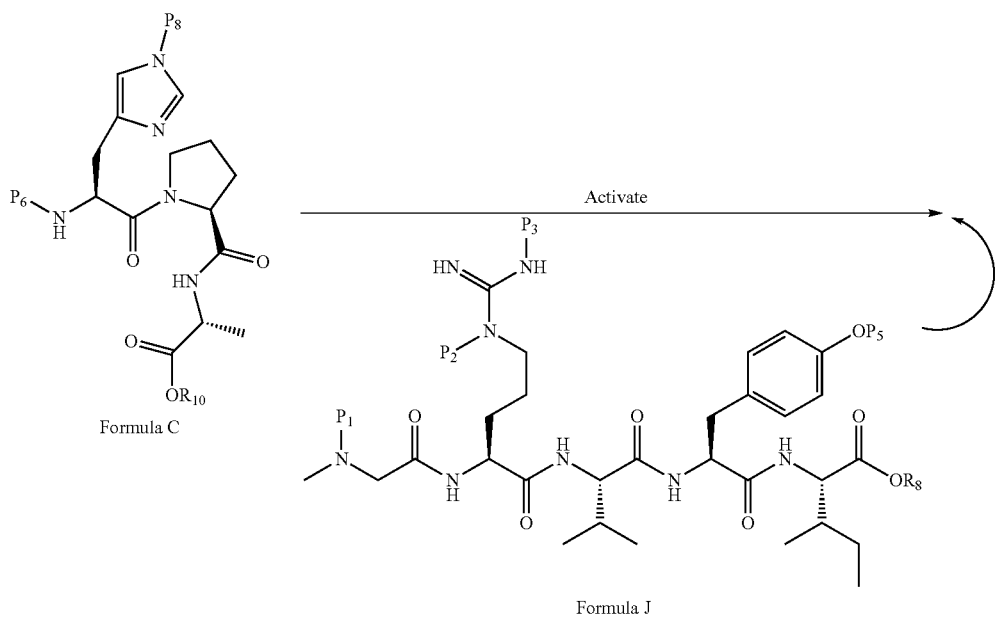

Formula C

Formula J

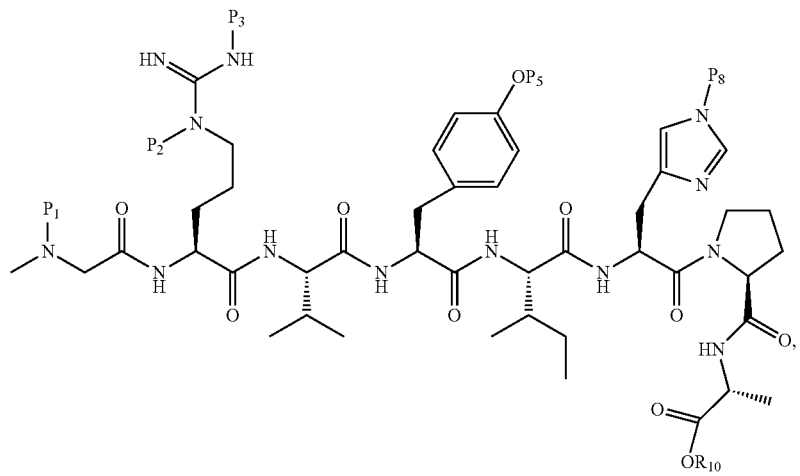

Formula H wherein the variables are as defined herein for the specific compounds. The conditions for preparing a compound of Formula H are described herein and, for example, in the examples. One of skill in the art can select the suitable activation agent for the appropriate scheme and compound produced according to the present disclosure and by reference to the specific examples contained herein. In some embodiments, a compound of Formula H is deprotected, (e.g. hydrogenated) to produce a compound of Formula 1. The hydrogenation can be performed, for example, in a solution of acetic acid (AcOH) as shown in some of the embodiments disclosed herein.

In some embodiments, methods of preparing a compound of Formula K

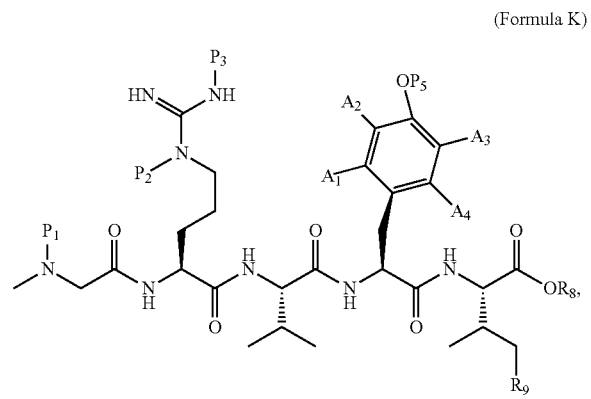

(Formula K)

are provided, wherein $P_1$ is a nitrogen protecting group such as but not limited to, Cbz, Fmoc, Boc, Alloc, TFA;

$P_2$ is H or a guanidine protecting group such as, but not limited to, $NO_2$, Boc, Cbz, Pbf;

$P_3$ is H or a guanidine protecting group such as, but not limited to, $NO_2$, Boc, Cbz, Pbf;

$P_5$ is H, tBu, Bom, TBS, allyl, Bn, or other commonly used protecting group for ethers or phenols; and $R_8$ is H, Me, Et, tBu, Bn, TMS or other protecting group for carboxylic acid;

$R_9$ is H or methyl;

$A_1$ is H, OH, F, $NO_2$, Cl, $CH_3$, or Br;

$A_2$ is H, OH, F, $NO_2$, Cl, $CH_3$, or Br;

$A_3$ is H, OH, F, $NO_2$, Cl, $CH_3$, or Br; and $A_4$ is H, OH, F, $NO_2$, Cl, $CH_3$, or Br.

In some embodiments, a compound of Formula K is prepared by contacting a compound of Formula A with a compound of Formula $B_1$ under conditions sufficient to produce a compound of Formula K. In some embodiments, a compound of Formula K is produced according to the following scheme:

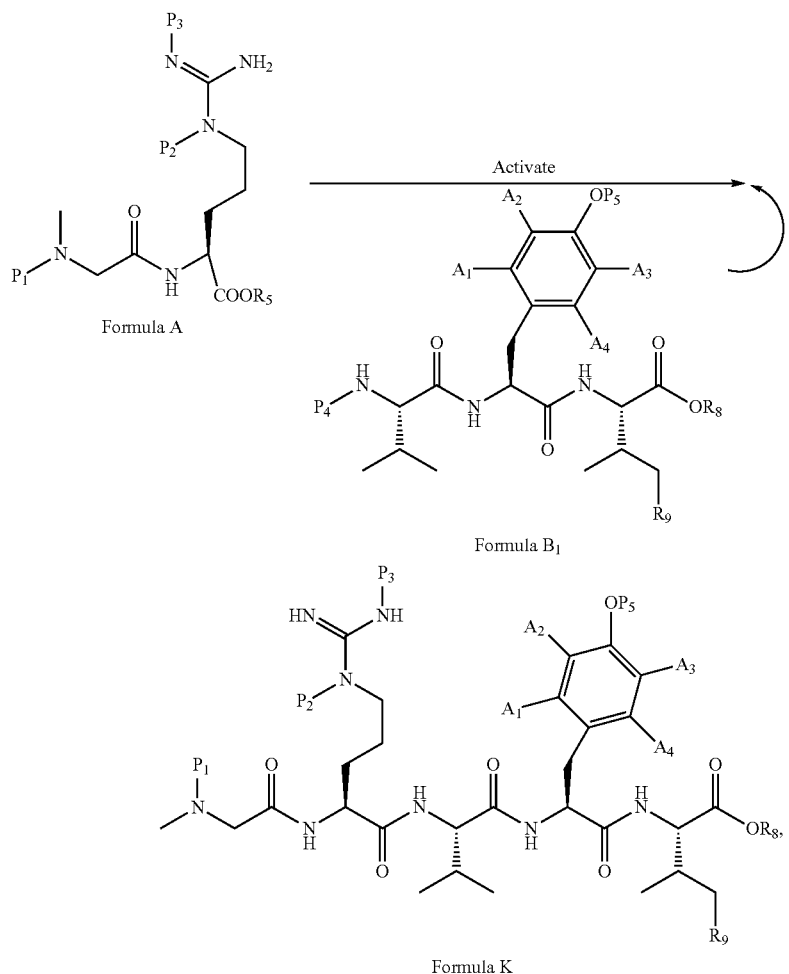

Formula A

Formula B₁

Formula K wherein the variables are as defined herein for the specific compounds. The conditions for preparing a compound of Formula K are described herein and, for example, in the examples. One of skill in the art can select the suitable activation agent for the appropriate scheme and compound produced according to the present disclosure and by reference to the specific examples contained herein.

In some embodiments, methods of preparing a compound of Formula L

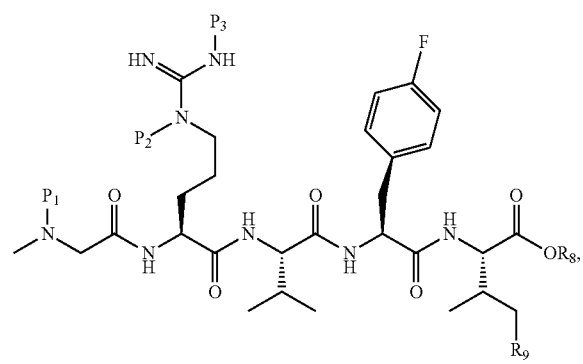

(L)

are provided, wherein $P_1$ is a nitrogen protecting group such as but not limited to, Cbz, Fmoc, Boc, Alloc, TFA;

$P_2$ is H or a guanidine protecting group such as, but not limited to, $NO_2$, Boc, Cbz, Pbf;

$P_3$ is H or a guanidine protecting group such as, but not limited to, $NO_2$, Boc, Cbz, Pbf;

$R_8$ is H, Me, Et, tBu, Bn, TMS or other protecting group for carboxylic acid; and $R_9$ is H or methyl.

In some embodiments, a compound of Formula L is prepared by contacting a compound of Formula A with a compound of Formula $B_2$ under conditions sufficient to produce a compound of Formula L. In some embodiments, a compound of Formula L is produced according to the following scheme:

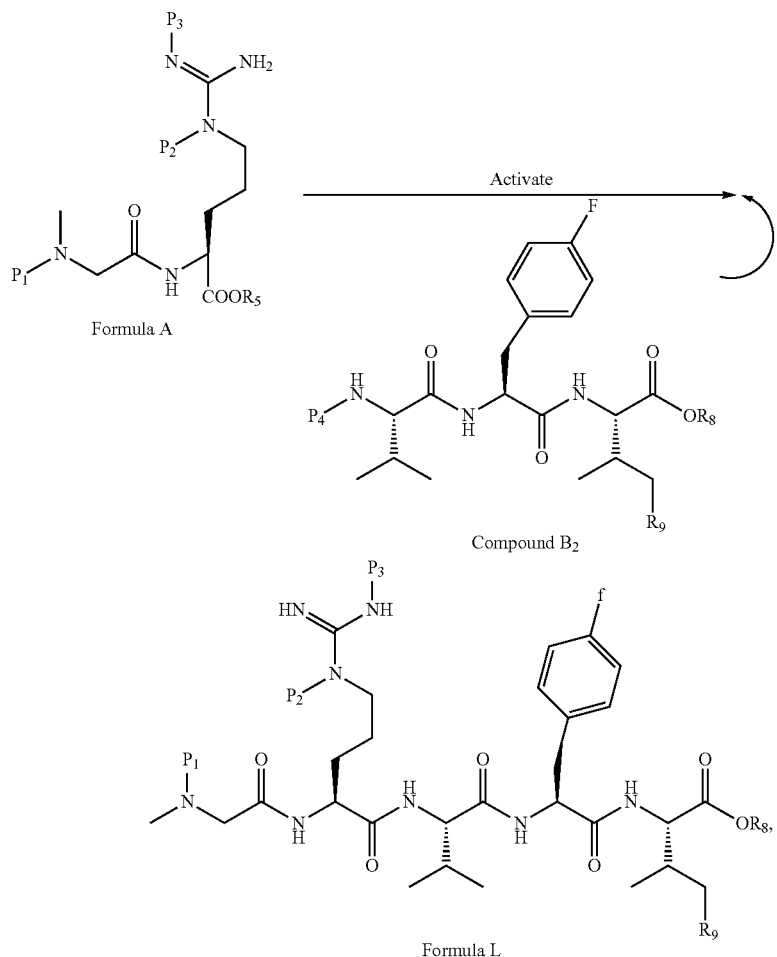

wherein the variables are as defined herein for the specific compounds. The conditions for preparing a compound of Formula L are described herein and, for example, in the examples. One of skill in the art can select the suitable activation agent for the appropriate scheme and compound produced according to the present disclosure and by reference to the specific examples contained herein.

In some embodiments, methods of preparing a compound of Formula M

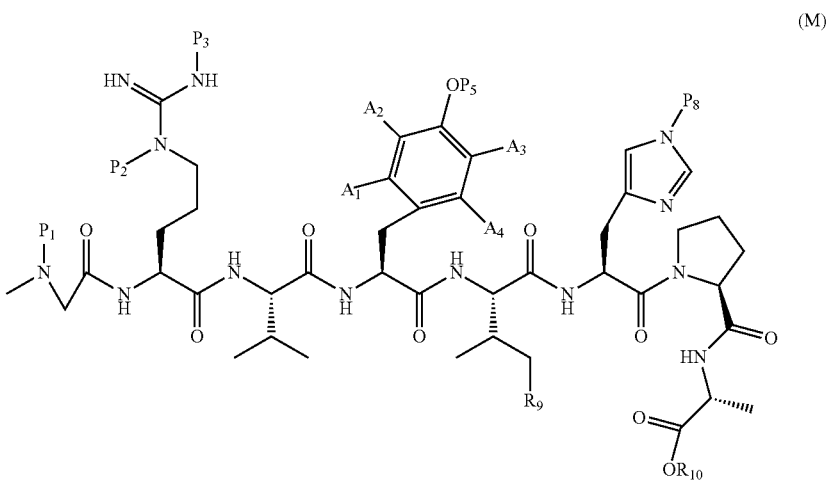

(M)

are provided, wherein
P$_1$ is a nitrogen protecting group such as but not limited to, Cbz, Fmoc, Boc, Alloc, TFA;
P$_2$ is H or a guanidine group such as, but not limited to, NO$_2$, Boc, Cbz, Pbf;
P$_3$ is H or a guanidine group such as, but not limited to, NO$_2$, Boc, Cbz, Pbf;
P$_5$ is H, tBu, Bom, TBS, allyl, Bn or other commonly used protecting group for ethers or phenols; and
P$_8$ is H, trityl, tBu, Bom, TBS or other commonly used protecting group for imidazoles;
R$_9$ is H or methyl;
R$_{10}$ is H, Me, Et, tBu, Bn, TMS or other protecting group for carboxylic acid;

A$_1$ is H, OH, F, NO$_2$, Cl, CH$_3$, or Br;
A$_2$ is H, OH, F, NO$_2$, Cl, CH$_3$, or Br;
A$_3$ is H, OH, F, NO$_2$, Cl, CH$_3$, or Br; and
A4 is H, OH, F, NO$_2$, Cl, CH$_3$, or Br,
wherein the method comprises contacting a compound of Formula K with a compound of Formula C under conditions sufficient to produce a compound of Formula M. A compound of Formula M can be hydrogenated to produce a compound of Formula 1 or Formula 1A depending upon the substituents on the compound of Formula K. The hydrogenation can be performed, for example, in acetic acid. In some embodiments, a compound of Formula M is prepared according to the following scheme:

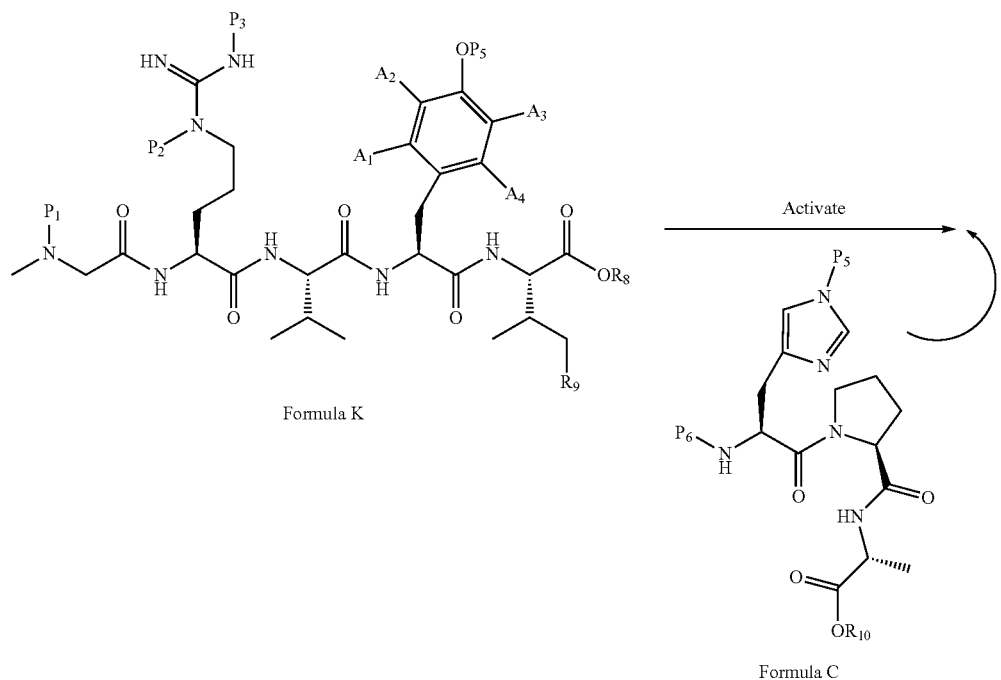

Formula K

Formula C

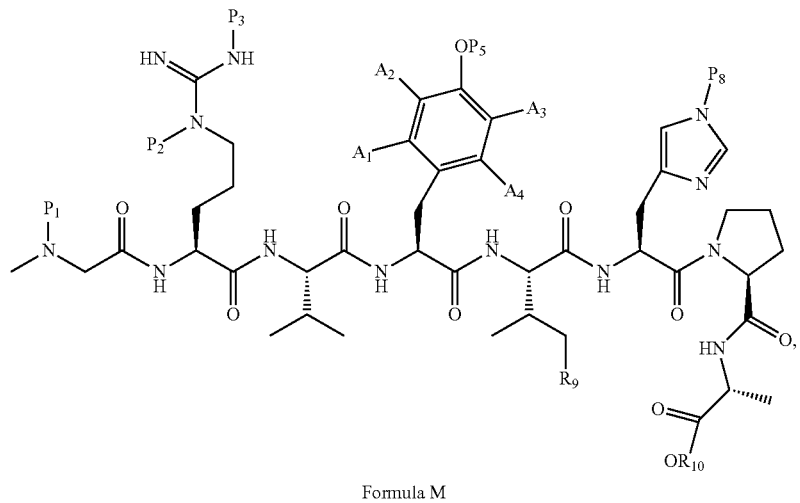

Formula M

The conditions for preparing a compound of Formula M are described herein and, for example, in the examples. One of skill in the art can select the suitable activation agent for the appropriate scheme and compound produced according to the present disclosure and by reference to the specific examples contained herein.

In some embodiments, a compound of Formula M is prepared according to a method comprising contacting a compound of Formula A with a compound of Formula F. In some embodiments, Formula A is activated using one of the activating agents described herein. In some embodiments, a compound of Formula M is prepared according to the following scheme:

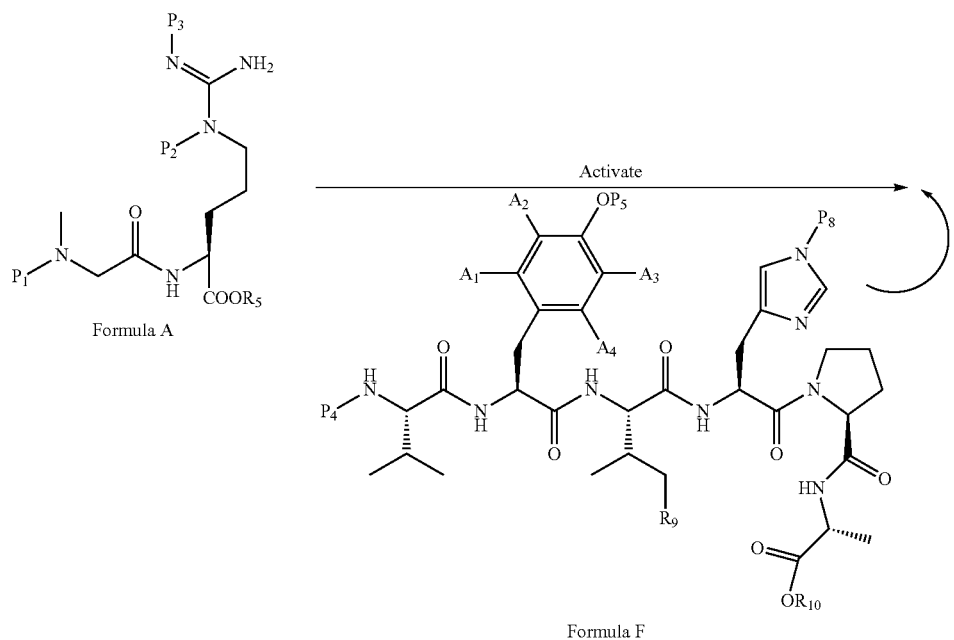

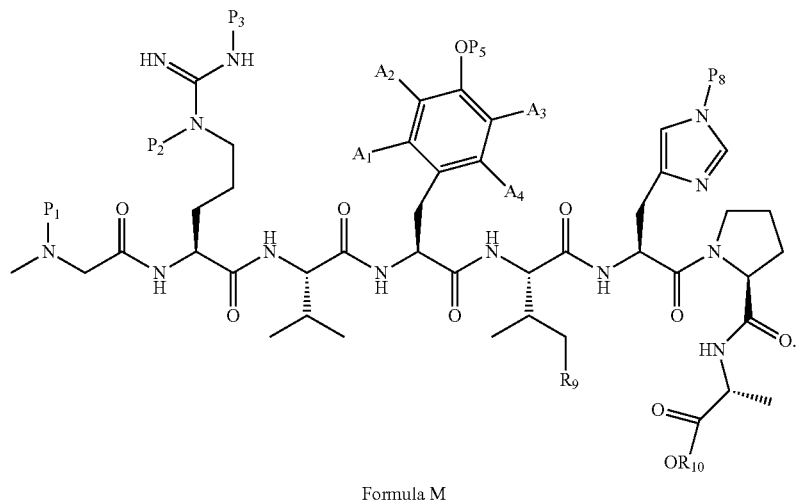

As discussed herein, a compound of Formula M can be deprotected, for example by hydrogenation, to produce a compound of Formula 1 or a compound of Formula 1A.

In addition to methods of preparing the various compounds described herein, the present embodiments also provide for compounds of the formula disclosed herein. Accordingly, in some embodiments, a compound is selected from the group consisting of a compound of Formula A, Formula B, Formula $B_1$, Formula $B_2$, Formula C, Formula D, Formula E, Formula F, Formula G, Formula H, Formula J, Formula K, Formula L, and Formula M is provided. In some embodiments, each of the compounds of the selected formula are contacted with an acid, e.g. HCl, to form an acid complex. Non-limiting examples of acid forms of the compounds are provided herein.

In some embodiments, compounds used in the synthesis are also provided. Accordingly, in some embodiments, a compound of the following formula are also provided:

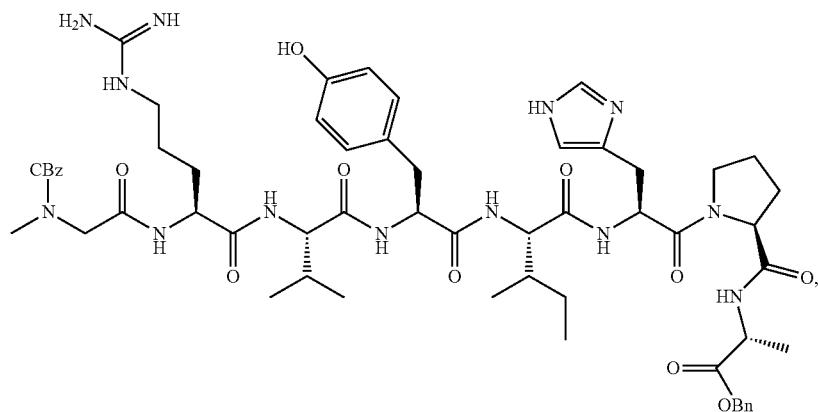

2

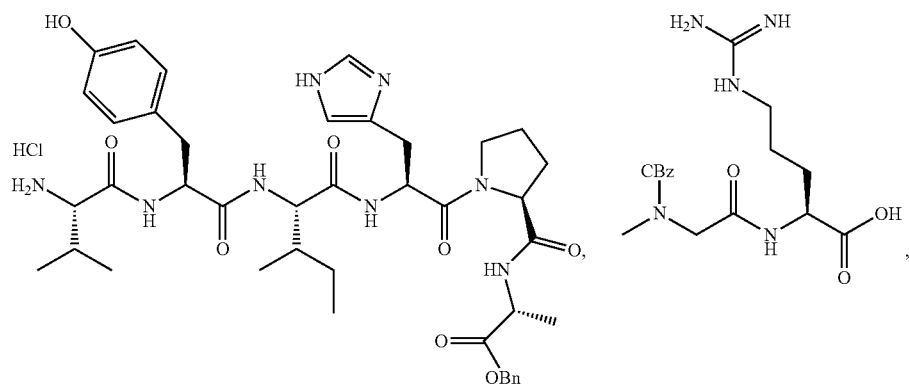

3

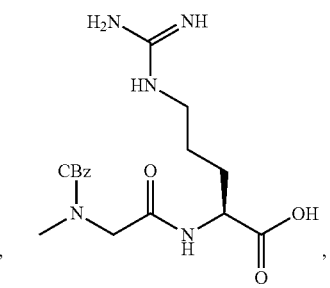

4

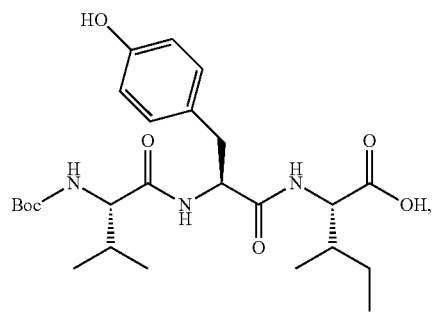

5

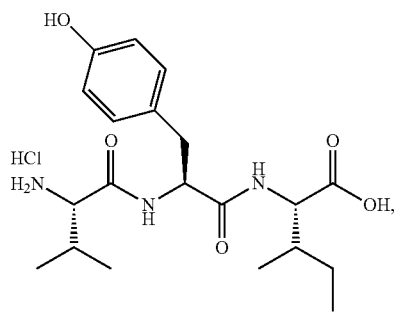

6

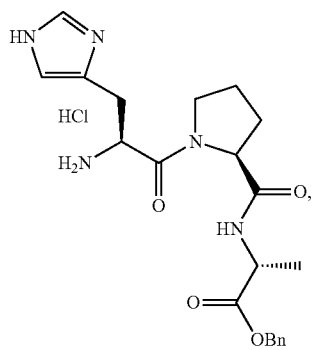

7

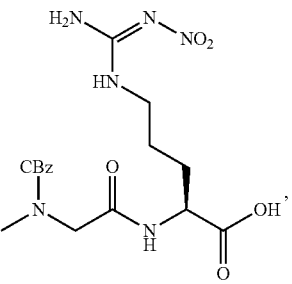

8

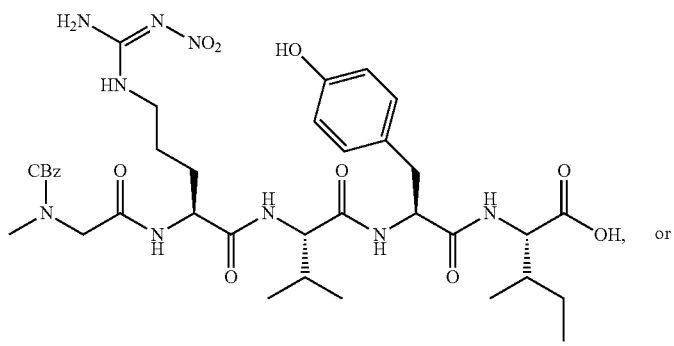

9 or

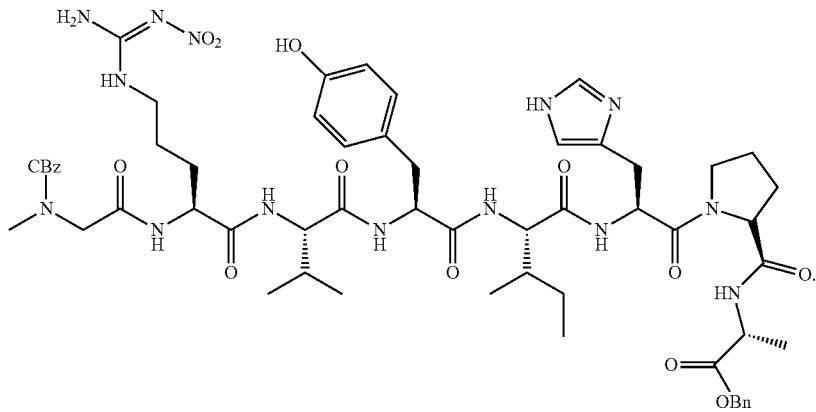

10

In some embodiments, SEQ ID NO: 1 is prepared according to scheme 1 (FIG. 1).

In some embodiments, the methods can comprise 1 or more, or all of the steps shown in scheme 1 (FIG. 1).

Figure 2:
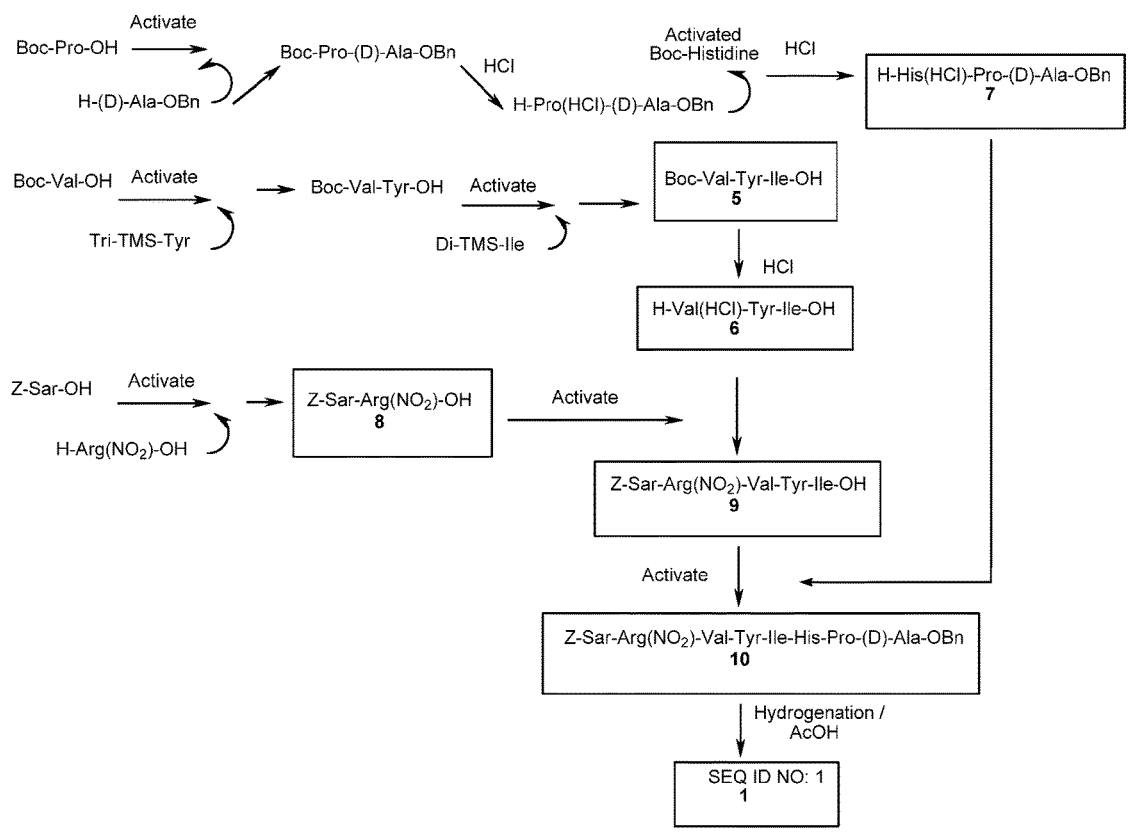
FIG. 2 depicts an exemplary scheme, Scheme 2, another process for preparing SEQ ID NO: 1.

In some embodiments, SEQ ID NO: 1 is prepared according to scheme 2 (FIG. 2).

In some embodiments, the methods can comprise 1 or more, or all of the steps shown in scheme 2 (FIG. 2).

In some embodiments, methods of preparing Sar-Arg-Val-Ww-Zz-His-Pro-(D)-Ala-OH (Formula 1A), are provided, wherein
  Ww is L-Tyr, 3-hydroxy-L-Tyr, 3-fluoro-L-Tyr, 2,6-difluoro-L-Tyr, 3-nitro-L-Tyr, 3,5-dinitro-L-tyrosine, 3-chloro-L-tyrosine, 2,6-dimethyl-L-tyrosine, 4-fluorophenyl-L-alanine, 3,5-dibromo-L-tyrosine, or O-allyl-L-tyrosine; and
  Zz is L-Val or L-Isoleucine.

Figure 3:
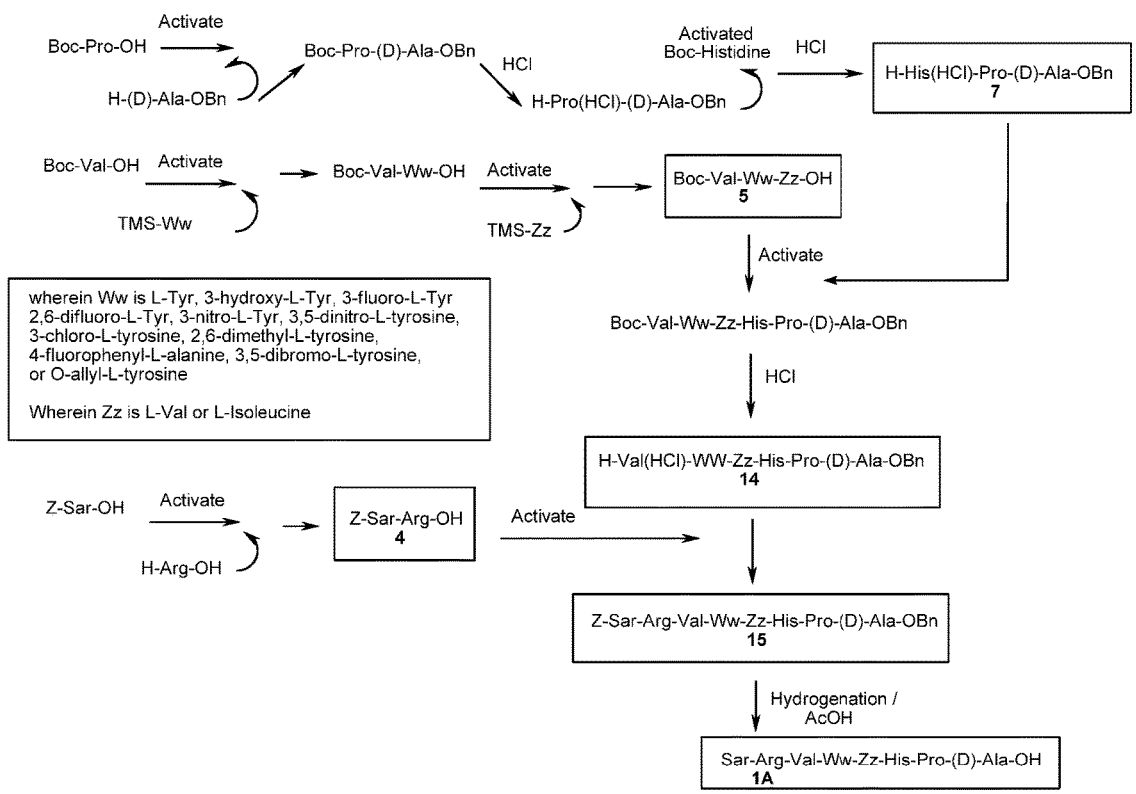
FIG. 3 depicts an exemplary scheme, Scheme 3, a process for preparing the compound of Formula 1A.

In some embodiments, the method of preparing Formula 1A comprises preparing the compound according to the scheme 3 (FIG. 3).

In some embodiments, the methods can comprise, 1 or more, or all of the steps shown in the scheme 3 (FIG. 3).

As discussed herein, Compound 1 can be prepared according to scheme 1 (FIG. 1) for assembly of the linear octapeptide. Schemes 2 (FIG. 2) and 3 (FIG. 3) can also be modified, for example, to achieve certain non-limiting objectives in terms of yield, quality, isolation process, and scalability of all intermediates. The schemes, for example, can employ the strategy of masking the amino and the carboxylic acid groups including its side chain functional group (Tyr, His) with TMS (via TMSCl) before coupling reaction. The TMS protecting group can eventually be cleaved during work up with aqueous HCl. This sequence, for example, saves steps and permitted the use of inexpensive amino acid as starting material. In some embodiments, the scheme is used to prepare intermediate compound 5 in multi grams scale and high yield. A similar strategy can also be used when coupling of intermediate Compound 7 with an activated subunit 5 or 9 (see, e.g., schemes 1, 2, 3). The flexibility of the temporary protecting strategy (scheme 3

(FIG. 3)) allows the synthesis of different subunits 5 where different amino acid, natural or unnatural, can be installed with ease and not have to worry about which protecting group to employ.

In some embodiments, compounds 4 (Z-SAR-Arg-OH) and 8 (Z-SAR-Arg(NO2)-OH) can be synthesized starting with a commercially available Z-Sarcosine. In some embodiments, pentafluorophenyl trifluoroacetate (TfaOPfp) can be used as a reagent for efficient coupling with unprotected Arginine or H-Arg(NO$_2$)—OH. In some embodiments, Z-SAR-OH is mixed in DCM with 1 equivalent of pyridine and PFP-trifluroacetate for about 2 hours before addition of NH$_4$Cl. In some embodiments, the mixture is washed with 5% HCl, bi-carbonate, and/or brine. In some embodiments, the resulting solution can be dried over Na$_2$SO$_4$ and concentrated under vacuum to provide Z-SAR-OPfp in quantitative yield and ready for coupling. In some embodiments, the composition is switched to a solvent of acetonitrile, L-arginine (0.9 eq) and 1 vol of water are added and the mixture is stirred for about 16 h. The mixture can be concentrated and solvent swapped to n-butanol. The resulting mixture can then be added to MTBE to precipitate compound 4 (90% yield). In some embodiments, compound 8 was synthesized the same way but with the addition of triethylamine since the solubility of Z-Sar-Arg(NO$_2$)—OH) is low in CH$_3$CN/H$_2$O.

In some embodiments, no protection for the highly basic guanidine group of argninine is required. The guanidine group of Arginine can be deactivated, for example, with 1 equivalent of acid (see, for example, scheme 5). In some embodiments, the combination of DCC and HOBt can be used under acidic condition when coupling with subunit 3 (see, for example, scheme 3 (FIG. 3)). In some embodiments, the deactivation method can also be generated in situ using the combination of BtH/SOCl$_2$ as a coupling reagent.

Scheme 5.

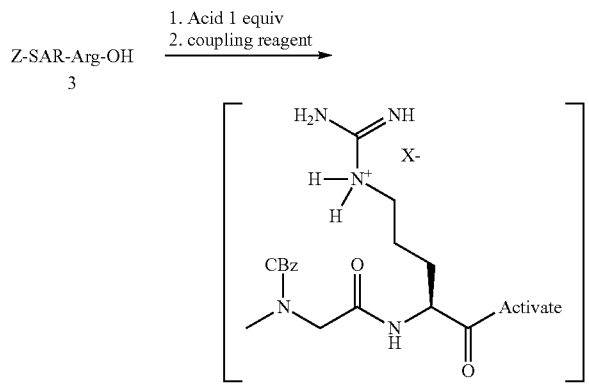

In some embodiments, the designed subunit 5 (Boc-Val-Tyr-Ile-OH) can be synthesized by solution phase employing a convergent strategy, which involves, for example, a mixed anhydride method employing the bis- and tris-TMS-amino acids (see, for example, scheme 7). Boc-Valine-OH can be converted to its mixed anhydride using EtOCOCl in presence of NMM at 0° C. and coupled with freshly prepared Tri-TMS-Tyrosine 16, which can be generated by the refluxing of the free Tyrosine in DCM with a mixture of TEA and TMSCl (3 eq). The reaction can be quenched with aqueous HCl and, in some embodiments, the organic layer can be washed with water. In some embodiments, the crude product 17 (Boc-Val-Tyr-OH) can be dried azeotropically and can be activated again to its mixed anhydride before coupling with another freshly prepared Di-TMS-Isoleusine 18. The reaction mixture can be stirred until the reaction is complete, and then quenched with aqueous acid (e.g., hydrochloric acid). The resulting solution can be washed with water and solvent swapped to MIBK. The solution can be cooled resulting in the crystallization of compound 5. The solid can be isolated by filtration, washed with cold MIBK and dried to give a white solid. The yield can be about 60-70% yield from Boc-Val-OH. In some embodiments, no column chromatography is used for the synthesis of 5. Even though there can be differences in the reactivity of different protecting groups (e.g., Boc vs. Fmoc), both processes work when employing the bis- and tris-TMS-amino acids (16 & 18). In some embodiments, pentafluorophenyl trifluoroacetate can be used to activate the carboxylic acid to pentafluorophenyl esters, which can be isolated and can be ready for coupling without purification.

Scheme 7: Synthesis of 5 (Boc-Val-Tyr-Ile-OH)

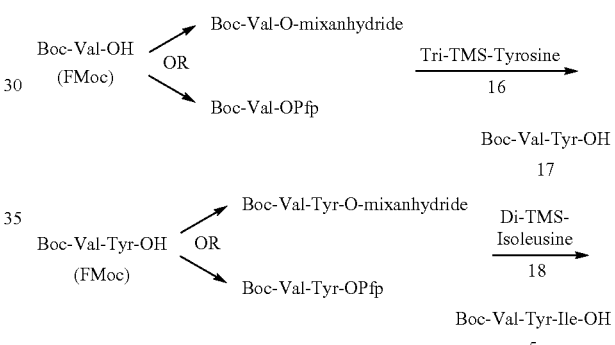

In some embodiments, the synthesis of H-His-Pro-(D)-Ala-OBn (7) relies on an N-acylbenzotriazoles for N-acylation. The report by Katrizky using the combination of BtH/SOCl$_2$ to activate the carboxylic acids especially for unprotected histidine can be applied to the procedure to Fmoc-His-OH for activation and subsequent coupling with H-Pro-(D)-Ala-OBn to provide compound 7 after deprotection using diethyl amine (DEA) at room temperature (see, for example, scheme 8). Preparation of 19 can be carried out by treating a mixture of four equivalents of 1H-benzotriazole and one equivalent of thionyl chloride in THF with Fmoc-His-OH at room temperature for about two hours. The white precipitate formed during the reaction can be filtered off, and the solvent can be completely removed under reduced pressure. The residue obtained can be dissolved in a minimum amount of DCM and can be subsequently used for the next reaction, which proceeded smoothly to provide protected Fmoc-His-Pro-(D)-Ala-OBn. In some embodiments, the use of Boc-His-OH can be used due to its low cost and deprotection can be done under acid conditions. In some embodiments, compound 7 can be made using Boc-His-OH. The use of DCC/HOBt provides another alternative. In some embodiments, Boc-deprotection via HCl/EtOAc can be used to produce 7 with a yield of about 90-100%.

Scheme 8: Synthesis of Compound 7

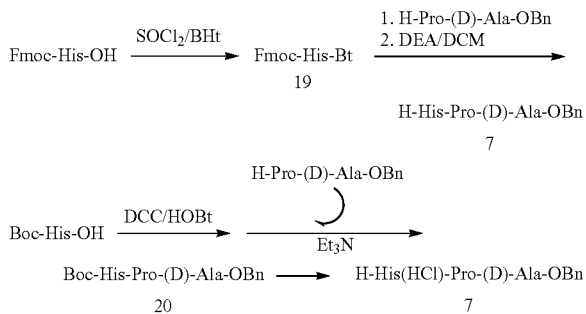

In some embodiments, coupling using DCC/HOBt and O, N-TMS-amino acids can be used for the extended synthesis of the hexapeptide 3 (see, for example, scheme 9). Boc-Val-Tyr-Ile-OH 5 can be activated via DCC/HOBt in DMF and coupled with freshly prepared Bis-TMS-His-Pro-(D)-Ala-OBn 21 to provide the protected hexapeptide, which can then be deprotected using HCl in EtOAc to give compound 3. Converting the resulting product 3 (H-Val(HCl)-Tyr-Ile-His-Pro-(D)-Ala-OBn) into Tri-TMS-hexapeptide which was directly used for coupling can be carried out in DCM in the presence of Et₃N and TMSCl (scheme 10).

In some embodiments, the final coupling step of the synthesis starts with the addition of 1 equivalent of acid (e.g. HCl) to deactivate the guanidine and converted to the monohydrochloride salt (scheme 10). In some embodiments, DCC/HOBt can be used under these conditions to give the coupling product 2 in a yield of about 35-50%. In some embodiments, the salt of the arginine generated through this method can also be carried to the end to give the corresponding salt of the final product. The resulting coupling product can be subjected to catalytic hydrogenation in alcohol (e.g., methanol) and acid (e.g. AcOH) to provide the final peptide, SEQ ID NO: 1 in good yield and high purity after crystallization.

Scheme 9: Synthesis of Compound 3

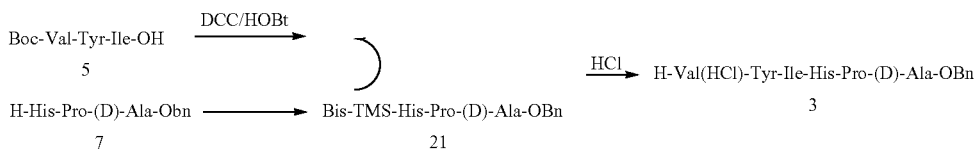

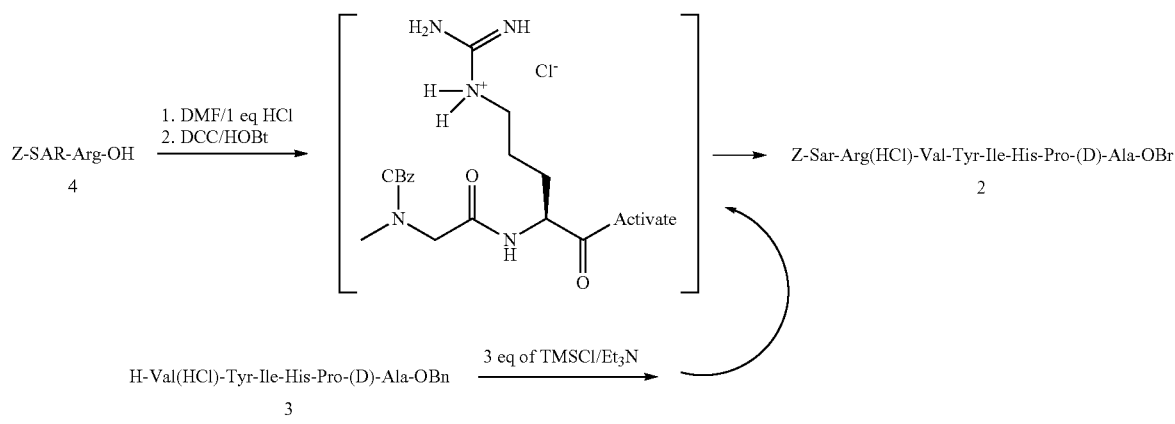

Scheme 10

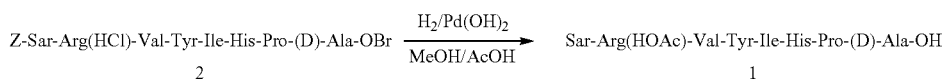

In some embodiments, compound 8 can be made readily available through two short steps similar to the synthesis of 4, and isolated as a white powder (85-95% overall yield) as described herein. In some embodiments, Z-Sar-Arg(NO$_2$)—OH can be activated via the combination of DCC and HOBt in DMF (see, for example, scheme 11, below). In some embodiments, after about 2 hours of stirring, compound 6 can be added followed by Et$_3$N and stirred for about 12-18 hours. The reaction mixture can be quenched with 5% acid (e.g. HCl) and extracted with EtOAc. In some embodiments, the organic layer can be washed with saturated salt (e.g., NaCl) solution, dried over sodium sulfate, and concentrated under reduced pressure to provide 9 (e.g. 75-90% yield after crystallization using MeOH:EtOAc). In some embodiments, the preparation of Compound 1 (SEQ ID NO: 1) can be then continued as described herein and as shown in Scheme 11.

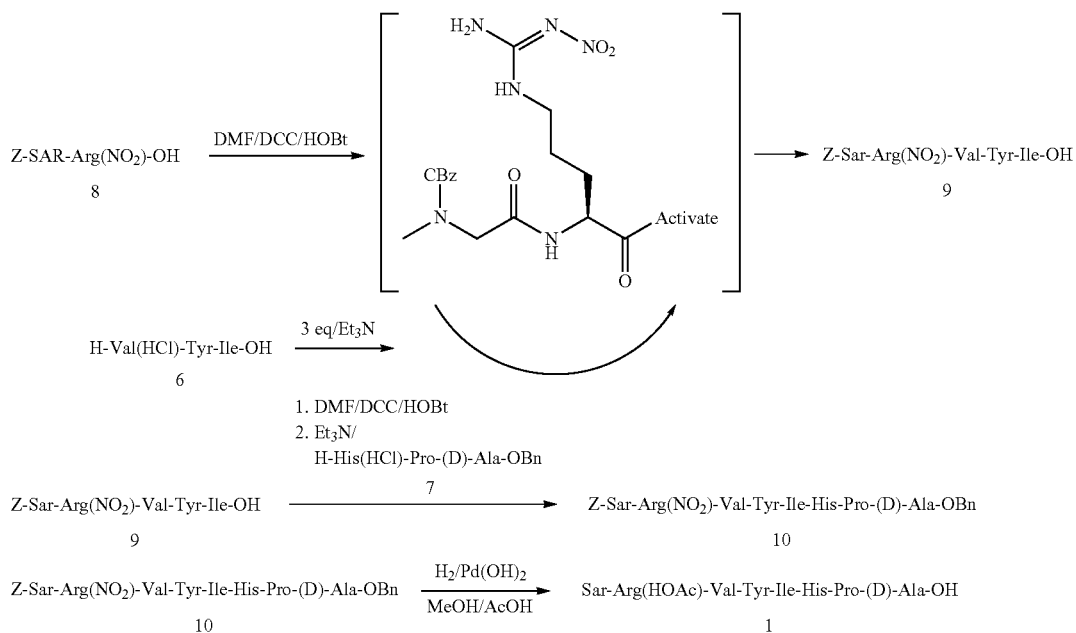

Scheme 11

The compounds prepared according to the methods described herein (e.g., Formula 1 or 1A) can be used, for example, in pharmaceutical compositions and formulations. The pharmaceutical compositions can be formulated by standard techniques using one or more physiologically acceptable carriers or excipients. In a some embodiments, the formulations may contain a buffer and/or a preservative. The compounds and their physiologically acceptable salts and solvates can be formulated for administration by any suitable route, including via inhalation, topically, nasally, orally, parenterally (e.g., intravenously, intraperitoneally, intravesically or intrathecally) or rectally in a vehicle comprising one or more pharmaceutically acceptable carriers, the proportion of which is determined by the solubility and chemical nature of the peptide, chosen route of administration and standard biological practice.

According to some embodiments, pharmaceutical compositions are provided comprising effective amounts of one or more compound(s) made according to the methods described herein together with, for example, pharmaceutically acceptable diluents, preservatives, solubilizers, emulsifiers, adjuvants and/or other carriers. Such compositions include diluents of various buffer content (e.g., TRIS or other amines, carbonates, phosphates, amino acids, for example, glycinamide hydrochloride (especially in the physiological pH range), N-glycylglycine, sodium or potassium phosphate (dibasic, tribasic), etc. or TRIS-HCl or acetate), pH and ionic strength; additives such as detergents and solubilizing agents (e.g., surfactants such as Pluronics, Tween 20, Tween 80 (Polysorbate 80), Cremophor, polyols such as polyethylene glycol, propylene glycol, etc.), antioxidants (e.g., ascorbic acid, sodium metabisulfite), preservatives (e.g., Thimersol, benzyl alcohol, parabens, etc.) and bulking substances (e.g., sugars such as sucrose, lactose, mannitol, polymers such as polyvinylpyrrolidones or dextran, etc.); and/or incorporation of the material into particulate preparations of polymeric compounds such as polylactic acid, polyglycolic acid, etc. or into liposomes. Hyaluronic acid may also be used. Such compositions can be employed to influence the physical state, stability, rate of in vivo release, and rate of in vivo clearance of a compound of the present invention. See, e.g., Remington's Pharmaceutical Sciences, 18th Ed. (1990, Mack Publishing Co., Easton, Pa. 18042) pages 1435-1712 which are herein incorporated by reference. The compositions can, for example, be prepared in liquid form, or can be in dried powder, such as lyophilized form. Particular methods of administering such compositions are described infra. The compositions can also be crystallized or precipitated. Examples of methods of crystallizing or precipitating can be found, for example, in U.S. Provisional Application No. 61/936,914, filed Feb. 7, 2014 and U.S. application Ser. No. 14/616,487, filed Feb. 6, 2015, each which is hereby incorporated by reference in its entirety.

Where a buffer is to be included in the formulations, the buffer can be selected from the group consisting of sodium acetate, sodium carbonate, citrate, glycylglycine, histidine, glycine, lysine, arginin, sodium dihydrogen phosphate, disodium hydrogen phosphate, sodium phosphate, and tris(hydroxymethyl)-aminomethan, or mixtures thereof. Each one of these specific buffers constitutes an alternative embodiment. In some embodiments the buffer is glycylglycine, sodium dihydrogen phosphate, disodium hydrogen phosphate, sodium phosphate or mixtures thereof.

Where a pharmaceutically acceptable preservative is to be included in the formulations of the invention, the preservative is selected from the group consisting of phenol, m-cresol, methyl p-hydroxybenzoate, propyl p-hydroxybenzoate, 2-phenoxyethanol, butyl p-hydroxybenzoate, 2-phenylethanol, benzyl alcohol, chlorobutanol, and thiomerosal, or mixtures thereof. Each one of these specific preservatives constitutes an alternative embodiment. In some embodiments, the preservative is phenol or m-cresol.

In some embodiments, the preservative is present in a concentration from about 0.1 mg/ml to about 50 mg/ml, in a concentration from about 0.1 mg/ml to about 25 mg/ml, or in a concentration from about 0.1 mg/ml to about 10 mg/ml.

The use of a preservative in pharmaceutical compositions is well-known to the skilled person. For convenience reference is made to Remington: The Science and Practice of Pharmacy, 19th edition, 1995.

In some embodiments, the formulation may further comprise a chelating agent where the chelating agent may be selected from salts of ethylenediaminetetraacetic acid (EDTA), citric acid, and aspartic acid, and mixtures thereof. Each one of these specific chelating agents constitutes an alternative embodiment.

In some embodiments, the chelating agent is present in a concentration from 0.1 mg/ml to 5 mg/ml. In some embodiments, the chelating agent is present in a concentration from 0.1 mg/ml to 2 mg/ml. In some embodiments, the chelating agent is present in a concentration from 2 mg/ml to 5 mg/ml.

The use of a chelating agent in pharmaceutical compositions is well-known to the skilled person. For convenience reference is made to Remington: The Science and Practice of Pharmacy, 19th edition, 1995.

In some embodiments, the formulation may further comprise a stabiliser selected from the group of high molecular weight polymers or low molecular compounds where such stabilizers include, but are not limited to, polyethylene glycol (e.g. PEG 3350), polyvinylalcohol (PVA), polyvinylpyrrolidone, carboxymethylcellulose, different salts (e.g. sodium chloride), L-glycine, L-histidine, imidazole, arginine, lysine, isoleucine, aspartic acid, tryptophan, threonine and mixtures thereof. Each one of these specific stabilizers constitutes an alternative embodiment. In some embodiments, the stabiliser is selected from the group consisting of L-histidine, imidazole and arginine.

In some embodiments, the high molecular weight polymer is present in a concentration from 0.1 mg/ml to 50 mg/ml. In some embodiments, the high molecular weight polymer is present in a concentration from 0.1 mg/ml to 5 mg/ml. In some embodiments, the high molecular weight polymer is present in a concentration from 5 mg/ml to 10 mg/ml. In some embodiments, the high molecular weight polymer is present in a concentration from 10 mg/ml to 20 mg/ml In some embodiments, the high molecular weight polymer is present in a concentration from 20 mg/ml to 30 mg/ml. In some embodiments, the high molecular weight polymer is present in a concentration from 30 mg/ml to 50 mg/ml.

In some embodiments, the low molecular weight compound is present in a concentration from 0.1 mg/ml to 50 mg/ml. In some embodiments, the low molecular weight compound is present in a concentration from 0.1 mg/ml to 5 mg/ml. In some embodiments, the low molecular weight compound is present in a concentration from 5 mg/ml to 10 mg/ml. In some embodiments, the low molecular weight compound is present in a concentration from 10 mg/ml to 20 mg/ml. In some embodiments, the low molecular weight compound is present in a concentration from 20 mg/ml to 30 mg/ml. In some embodiments, the low molecular weight compound is present in a concentration from 30 mg/ml to 50 mg/ml.

The use of a stabilizer in pharmaceutical compositions is well-known to the skilled person. For convenience reference is made to Remington: The Science and Practice of Pharmacy, 19th edition, 1995.

In some embodiments, the formulation of the invention may further comprise a surfactant where a surfactant may be selected from a detergent, ethoxylated castor oil, polyglycolyzed glycerides, acetylated monoglycerides, sorbitan fatty acid esters, poloxamers, such as 188 and 407, polyoxyethylene sorbitan fatty acid esters, polyoxyethylene derivatives such as alkylated and alkoxylated derivatives (tweens, e.g. Tween-20, or Tween-80), monoglycerides or ethoxylated derivatives thereof, diglycerides or polyoxyethylene derivatives thereof, glycerol, cholic acid or derivatives thereof, lecithins, alcohols and phospholipids, glycerophospholipids (lecithins, kephalins, phosphatidyl serine), glyceroglycolipids (galactopyransoide), sphingophospholipids (sphingomyelin), and sphingoglycolipids (ceramides, gangliosides), DSS (docusate sodium, docusate calcium, docusate potassium, SDS (sodium dodecyl sulfate or sodium lauryl sulfate), dipalmitoyl phosphatidic acid, sodium caprylate, bile acids and salts thereof and glycine or taurine conjugates, ursodeoxycholic acid, sodium cholate, sodium deoxycholate, sodium taurocholate, sodium glycocholate, N-Hexadecyl-N,N-dimethyl-3-ammonio-1-propanesulfonate, anionic (alkyl-aryl-sulphonates) monovalent surfactants, palmitoyl lysophosphatidyl-L-serine, lysophospholipids (e.g. 1-acyl-sn-glycero-3-phosphate esters of ethanolamine, choline, serine or threonine), alkyl, alkoxyl (alkyl ester), alkoxy (alkyl ether)-derivatives of lysophosphatidyl and phosphatidylcholines, e.g. lauroyl and myristoyl derivatives of lysophosphatidylcholine, dipalmitoylphosphatidylcholine, and modifications of the polar head group, that is cholines, ethanolamines, phosphatidic acid, serines, threonines, glycerol, inositol, and the postively charged DODAC, DOTMA, DCP, BISHOP, lysophosphatidylserine and lysophosphatidylthreonine, zwitterionic surfactants (e.g. N-alkyl-N,N-dimethylammonio-1-propanesulfonates, 3-cholamido-1-propyldimethylammonio-1-propanesulfonate, dodecylphosphocholine, myristoyl lysophosphatidylcholine, hen egg lysolecithin), cationic surfactants (quarternary ammonium bases) (e.g. cetyl-trimethylammonium bromide, cetylpyridinium chloride), non-ionic surfactants, polyethyleneoxide/polypropyleneoxide block copolymers (Pluronics/Tetronics, Triton X-100, Dodecyl β-D-glucopyranoside) or polymeric surfactants (Tween-40, Tween-80, Brij-35), fusidic acid derivatives—(e.g. sodium tauro-dihydrofusidate etc.), long-chain fatty acids and salts thereof C6-C12 (e.g. oleic acid and caprylic acid), acylcarnitines and derivatives, Nα-acylated derivatives of lysine, arginine or histidine, or side-chain acylated derivatives of lysine or arginine, Nα-acylated derivatives of dipeptides comprising any combination of lysine, arginine or histidine and a neutral or acidic amino acid, Nα-acylated derivative of a tripeptide comprising any combination of a neutral amino acid and two charged amino acids, or the surfactant may be selected from the group of imidazoline derivatives, or mixtures thereof. Each one of these specific surfactants constitutes an alternative embodiment of the invention.

The use of a surfactant in pharmaceutical compositions is well-known to the skilled person. For convenience reference is made to Remington: The Science and Practice of Pharmacy, 19th edition, 1995.

Pharmaceutically acceptable sweeteners comprise preferably at least one intense sweetener such as saccharin, sodium or calcium saccharin, aspartame, acesulfame potassium, sodium cyclamate, alitame, a dihydrochalcone sweetener, monellin, stevioside or sucralose (4,1',6'-trichloro-4,1',6'-trideoxygalactosucrose), preferably saccharin, sodium or calcium saccharin, and optionally a bulk sweetener such as sorbitol, mannitol, fructose, sucrose, maltose, isomalt, glucose, hydrogenated glucose syrup, xylitol, caramel or honey.

Intense sweeteners are conveniently employed in low concentrations. For example, in the case of sodium saccharin, the concentration may range from 0.04% to 0.1% (w/v) based on the total volume of the final formulation, and preferably is about 0.06% in the low-dosage formulations and about 0.08% in the high-dosage ones. The bulk sweetener can effectively be used in larger quantities ranging from about 10% to about 35%, preferably from about 10% to 15% (w/v).

The formulations of the invention may be prepared by conventional techniques, e.g. as described in Remington's Pharmaceutical Sciences, 1985 or in Remington: The Science and Practice of Pharmacy, 19th edition, 1995, where such conventional techniques of the pharmaceutical industry involve dissolving and mixing the ingredients as appropriate to give the desired end product.

The compounds described herein can also be administered by any method known in the art. For example, administration may be transdermal, parenteral, intravenous, intra-arterial, subcutaneous, intramuscular, intracranial, intraorbital, ophthalmic, intraventricular, intracapsular, intraspinal, intracisternal, intraperitoneal, intracerebroventricular, intrathecal, intranasal, aerosol, by suppositories, or oral administration. In some embodiments, a pharmaceutical composition of the compounds prepared herein can be for administration for injection, or for oral, pulmonary, nasal, transdermal, ocular administration.

For oral administration, the peptide or a therapeutically acceptable salt thereof can be formulated in unit dosage forms such as capsules or tablets. The tablets or capsules may be prepared by conventional means with pharmaceutically acceptable excipients, including binding agents, for example, pregelatinised maize starch, polyvinylpyrrolidone, or hydroxypropyl methylcellulose; fillers, for example, lactose, microcrystalline cellulose, or calcium hydrogen phosphate; lubricants, for example, magnesium stearate, talc, or silica; disintegrants, for example, potato starch or sodium starch glycolate; or wetting agents, for example, sodium lauryl sulphate. Tablets can be coated by methods well known in the art. Liquid preparations for oral administration can take the form of, for example, solutions, syrups, or suspensions, or they can be presented as a dry product for constitution with water or other suitable vehicle before use. Such liquid preparations can be prepared by conventional means with pharmaceutically acceptable additives, for example, suspending agents, for example, sorbitol syrup, cellulose derivatives, or hydrogenated edible fats; emulsifying agents, for example, lecithin or acacia; non-aqueous vehicles, for example, almond oil, oily esters, ethyl alcohol, or fractionated vegetable oils; and preservatives, for example, methyl or propyl-p-hydroxybenzoates or sorbic acid. The preparations can also contain buffer salts, flavoring, coloring, and/or sweetening agents as appropriate. If desired, preparations for oral administration can be suitably formulated to give controlled release of the active compound. The compounds can also be prepared with cyclodextrins or other large molecules to facilitate oral adsorption.

For topical administration, the peptide can be formulated in a pharmaceutically acceptable vehicle containing 0.1 to 10 percent or 0.5 to 5 percent of the active compound(s). Such formulations can be in the form of a cream, lotion, sublingual tablet, aerosols and/or emulsions and can be included in a transdermal or buccal patch of the matrix or reservoir type as are conventional in the art for this purpose.

For parenteral administration, the compounds of the present invention are administered by either intravenous, subcutaneous, or intramuscular injection, in compositions with pharmaceutically acceptable vehicles or carriers. The compounds can be formulated for parenteral administration by injection, for example, by bolus injection or continuous infusion. Formulations for injection can be presented in unit dosage form, for example, in ampoules or in multi-dose containers, with an added preservative. The compositions can take such forms as suspensions, solutions, or emulsions in oily or aqueous vehicles, and can contain formulatory agents, for example, suspending, stabilizing, and/or dispersing agents. Alternatively, the active ingredient can be in powder form for constitution with a suitable vehicle, for example, sterile pyrogen-free water, before use.

For administration by injection, it is preferred to use the compound(s) in solution in a sterile aqueous vehicle which may also contain other solutes such as buffers or preservatives as well as sufficient quantities of pharmaceutically acceptable salts or of glucose to make the solution isotonic. In some embodiments, the pharmaceutical compositions of the present invention may be formulated with a pharmaceutically acceptable carrier to provide sterile solutions or suspensions for injectable administration. In particular, injectables can be prepared in conventional forms, either as liquid solutions or suspensions, solid forms suitable for solution or suspensions in liquid prior to injection or as emulsions. Suitable excipients are, for example, water, saline, dextrose, mannitol, lactose, lecithin, albumin, sodium glutamate, cysteine hydrochloride, or the like. In addition, if desired, the injectable pharmaceutical compositions may contain minor amounts of nontoxic auxiliary substances, such as wetting agents, pH buffering agents, and the like. If desired, absorption enhancing preparations (e.g., liposomes) may be utilized. Suitable pharmaceutical carriers are described in "Remington's pharmaceutical Sciences" by E. W. Martin.

For administration by inhalation, the compounds may be conveniently delivered in the form of an aerosol spray presentation from pressurized packs or a nebulizer, with the use of a suitable propellant, for example, dichlorodifluoromethane, trichlorofluoromethane, dichlorotetrafluoroethane, carbon dioxide, or other suitable gas. In the case of a pressurized aerosol, the dosage unit can be determined by providing a valve to deliver a metered amount. Capsules and cartridges of, for example, gelatin for use in an inhaler or insufflator can be formulated containing a powder mix of the compound and a suitable powder base, for example, lactose or starch. For intranasal administration the compounds of the invention may be used, for example, as a liquid spray, as a powder or in the form of drops.

The compounds can also be formulated in rectal compositions, for example, suppositories or retention enemas, for example, containing conventional suppository bases, for example, cocoa butter or other glycerides.

Furthermore, the compounds can be formulated as a depot preparation. Such long-acting formulations can be administered by implantation (for example, subcutaneously or intramuscularly) or by intramuscular injection. Thus, for example, the compounds can be formulated with suitable polymeric or hydrophobic materials (for example as an emulsion in an acceptable oil) or ion exchange resins, or as sparingly soluble derivatives, for example, as a sparingly soluble salt.

The compositions can, if desired, be presented in a pack or dispenser device that can contain one or more unit dosage forms containing the active ingredient. The pack can, for example, comprise metal or plastic foil, for example, a blister pack. The pack or dispenser device can be accompanied by instructions for administration.

The compounds prepare according to the methods described herein may be administered to a patient at therapeutically effective doses to prevent, treat, or control diseases and disorders mediated, in whole or in part, by a GPCR-ligand interaction of the present invention. Pharmaceutical compositions comprising one or more of compounds described herein may be administered to a patient in an amount sufficient to elicit an effective protective or therapeutic response in the patient. An amount adequate to accomplish this is defined as "therapeutically effective dose." The dose will be determined by the efficacy of the particular compound employed and the condition of the subject, as well as the body weight or surface area of the area to be treated. The size of the dose also will be determined by the existence, nature, and extent of any adverse effects that accompany the administration of a particular compound or vector in a particular subject.

Toxicity and therapeutic efficacy of such compounds can be determined by standard pharmaceutical procedures in cell cultures or experimental animals, for example, by determining the LD50 (the dose lethal to 50% of the population) and the ED50 (the dose therapeutically effective in 50% of the population). The dose ratio between toxic and therapeutic effects is the therapeutic index and can be expressed as the ratio, LD50/ED50. Compounds that exhibit large therapeutic indices are preferred. While compounds that exhibit toxic side effects can be used, care should be taken to design a delivery system that targets such compounds to the site of affected tissue to minimize potential damage to normal cells and, thereby, reduce side effects.

The data obtained from cell culture assays and animal studies can be used to formulate a dosage range for use in humans. The dosage of such compounds lies preferably within a range of circulating concentrations that include the ED50 with little or no toxicity. The dosage can vary within this range depending upon the dosage form employed and the route of administration. For any compound used in the methods of the invention, the therapeutically effective dose can be estimated initially from cell culture assays. A dose can be formulated in animal models to achieve a circulating plasma concentration range that includes the IC50 (the concentration of the test compound that achieves a half-maximal inhibition of symptoms) as determined in cell culture. Such information can be used to more accurately determine useful doses in humans. Levels in plasma can be measured, for example, by high performance liquid chromatography (HPLC). In general, the dose equivalent of a modulator is from about 1 ng/kg to 10 mg/kg for a typical subject.

The amount and frequency of administration of the compounds of the invention and/or the pharmaceutically acceptable salts thereof will be regulated according to the judgment of the attending clinician considering such factors as age, condition and size of the patient as well as severity of the symptoms being treated. An ordinarily skilled physician or veterinarian can readily determine and prescribe the effective amount of the drug required to prevent, counter or arrest the progress of the condition. In general it is contemplated that an effective amount would be from 0.001 mg/kg to 10 mg/kg body weight, and in particular from 0.01 mg/kg to 1 mg/kg body weight. More specifically it is contemplated that an effective amount would be to continuously infuse by intravenous administration from 0.01 micrograms/kg body weight/min to 100 micrograms/kg body weight/min for a period of 12 hours to 14 days. It may be appropriate to administer the required dose as two, three, four or more sub-doses at appropriate intervals throughout the day. Said sub-doses may be formulated as unit dosage forms, for example, containing 0.01 to 500 mg, and in particular 0.1 mg to 200 mg of active ingredient per unit dosage form.

In some embodiments, the pharmaceutical preparation is in a unit dosage form. In such form, the preparation is subdivided into suitably sized unit doses containing appropriate quantities of the active component, e.g., an effective amount to achieve the desired purpose. The quantity of active compound in a unit dose of preparation may be varied or adjusted from about 0.01 mg to about 1000 mg, preferably from about 0.01 mg to about 750 mg, more preferably from about 0.01 mg to about 500 mg, and most preferably from about 0.01 mg to about 250 mg, according to the particular application. The actual dosage employed may be varied depending upon the requirements of the patient and the severity of the condition being treated. Determination of the proper dosage regimen for a particular situation is within the skill of the art. For convenience, the total dosage may be divided and administered in portions during the day as required.

A composition comprising a compound described herein or prepared according to a method described herein can be used for treating a cardiovascular or cardiorenal disorder that, for example, would respond favorably to a decrease in blood pressure.

In some embodiments, methods of treating cardiovascular disorders with a compound described herein are provided. In some embodiments, the method comprises administering to a subject, or a subject in need thereof, a therapeutically effective amount of a compound described herein and/or pharmaceutically acceptable salt thereof. In some embodiments, the method comprises administering to a subject, or a subject in need thereof, a therapeutically effective amount of SEQ ID. NO. 1 prepared according to a method described herein and/or pharmaceutically acceptable salt thereof. These cardiovascular disorders include, but are not limited to, chronic hypertension, hypertensive crisis, acute congestive heart failure, angina, acute myocardial infarction, left ventricular failure, cerebrovascular insufficiency, intracranial haemorrhage, heart failure, acute decompensated heart failure, which can also be referred to as acute heart failure, essential hypertension, post-operative hypertension, hypertensive heart disease, hypertensive renal disease, renovascular hypertension, malignant hypertension, post-renal transplant patient stabilization, dilated cardiomyopathy, myocarditis, post-cardiac transplant patient stabilization, disorders associated with post-stent management, neurogenic hypertension, pre-eclampsia, abdominal aortic aneurysm, and any cardiovascular disorder with a hemodynamic component.

In some embodiments, the cardiovascular disorder is an acute cardiovascular disorder. In some embodiments, the acute cardiovascular disorder is acute hypertensive crisis, toxemia of pregnancy, acute myocardial infarction, acute congestive heart failure, acute heart failure, acute ischaemic heart disease, pulmonary hypertension, post-operative hypertension, migraine, retinopathy and post-operative cardiac/valve surgery.

In some embodiments, methods of treating viral infectious disease linked to AT1R are provided. In some embodiments, the methods comprise administering to a subject in need thereof a therapeutically effective amount of crystalline Form I and/or pharmaceutically acceptable salt thereof. In specific embodiments, the composition is administered by intravenous injection.

The compounds described herein have shown to be useful in treating such disorders. For example, the compounds have been shown to be useful for the treatment of such disorders in U.S. Pat. No. 8,486,885, Soergel D G, et al., J Clin Pharmacol. 2013 September; 53(9):892-9, Violin et al., Trends Cardiovasc Med. 2013 October; 23(7):242-9, and Violin et al., J Pharmacol Exp Ther. 2010 December; 335(3):572-9, each of which is incorporated by reference in its entirety.

EXAMPLES

Example 1

Preparation of Z-Sar-Arg-OH (4)

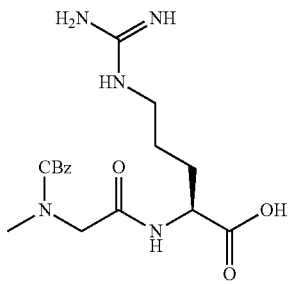

Pyridine (1.1 eq, 49.3 mmol, 3.97 ml) and pentafluorophenyl trifluoroacetate (1.2 eq, 53.8 mmol, 9.24 ml) were added to a solution of Z-Sar-OH (10.0 g, 44.8 mmol) in DCM (120 ml) at 0° C. The reaction mixture was allowed to warm to room for 2 hours then quenched with sat. $NH_4Cl$ (70 ml), washed with water (2×70 ml), brine, dried over $Na_2SO_4$, and concentrated under reduced pressure to provide Z-Sar-OPfp in quantitative yield.

A solution of L-arginine (0.9 eq, 40.3 mmol, 7.04 g) in 50 ml of water was added to the crude product prepared above (in 235 ml of acetonitrile) at room temperature. The reaction mixture was stirred at room temperature overnight before concentrated to dryness. 40 ml of n-BuOH was added at the end of concentration to remove water. The crude mixture was dissolved in 50 ml of MeOH and slowly added to MTBE (1.5 L) while stirring to precipitate product. Filtered and dried in vacuum at 40° C. overnight to give 13.75 g (90% over all yield): (HPLC Purity=88.10%)); m/z (ES+) 380.42

Example 2

Preparation of Boc-Val-Tyr-Ile-OH (5)

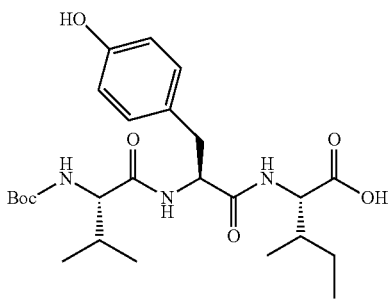

To a solution of Boc-Valine (1.74 g, 8 mmol) in THF (40 ml) is added N-methylmorpholine (1.1 eq, 8.8 mmol, 0.97 ml). The mixture is cooled to 0° C. and ethylchlorofomate (1.1 eq, 8.8 mmol, 0.85 ml) is added. The reaction was stirred for 30 min at 0° C.

In a separate vessel, tyrosine (1.5 eq, 12.0 mmol, 2.17 g), trimethylsilylchloride (3.08 eq, 36.9 mmol, 4.68 ml)) and TEA (3.08 eq, 36.9 mmol, 5.13 ml) are refluxed in DCM for 2.5 hours. The resulting solution was cooled and added to the Boc valine mixed anhydride at 0° C. that prepared earlier. The solution is stirred until the reaction is complete. The reaction is quenched with 5% HCl (100 ml) and stirred at room temperature for 30 minutes. Layers were separated; aqueous layer was extracted with DCM (2×50 ml). Combined organic extract was washed with water (100 ml), brine (50 ml) and dried over anhydrous $Na_2SO_4$. Solvent was evaporated in vacuum, and solvent swapped to THF.

N-methylmorpholine (1.1 eq, 8.69 mmol, 0.96 ml) is added and the mixture is cooled to 0° C. Ethyl chloroformate (1.1 eq, 8.69 mmol, 0.83 ml) is added to form the mixed anhydride (30 minutes at 0° C.).

In a separate vessel, isoleucine (1.5 eq, 11.84 mmol, 1.55 g), trimethylsilylchloride (2.05 eq, 24.27 mmol, 3.1 ml)) and TEA (2.05 eq, 24.27 mmol, 3.38 ml) are refluxed in DCM for 2.5 hours. The resulting solution was cooled and added to the mixed anhydride solution at 0° C. The reaction mixture was stirred until the reaction is complete, and then quenched with aqueous hydrochloric acid (100 ml) and stirred at room temperature for 30 minutes. Layers were separated; aqueous layer was extracted with DCM (2×50 ml). Combined organic extract was washed with water (100 ml), brine (50 ml) and dried over anhydrous $Na_2SO_4$. Solvent was evaporated in vacuum, and solvent swapped to MIBK.

The resulting solution is washed with water and solvent swapped to MIBK. The solution is cooled resulting in the crystallization of the title compound. The solid is isolated by filtration, washed with cold MIBK and dried to give a white solid (67% overall yield from Boc-Val-OH): (HPLC Purity=98.4%)); m/z (ES+) 494.61

Example 3

Preparation of Val(HCl)-Tyr-Ile-OH (6)

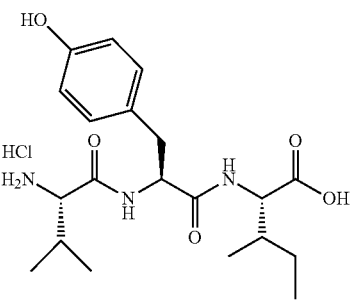

6

5 eq of HCl in EtOAc was added slowly to a heterogeneous solution of Boc-Val-Tyr-Ile-OH (5) (2.5 g, 5.075 mmol) in EtOAc (12 ml). The reaction mixture was stirred overnight before filtered and washed with MTBE to give 2.11 g (97%) of the title compound: (HPLC Purity=97.8%)); m/z (ES+) 394.61

Example 4

Preparation of H-Pro(HCl)-(D)Ala-OBn

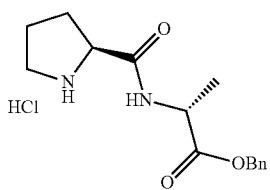 [SMILES: Cl ; C[C@@H](NC(=O)[C@@H]1CCCN1)C(=O)OCc1ccccc1]

N-methylmorpholine (1.19 eq, 101.6 mmol, 11.2 ml) was added to a solution of Boc-Pro-OH in THF (355 ml) at room temperature followed by the addition of ethylchloroformate (1.05 eq, 89.65 mmol, 8.58 ml). The cloudy solution was stirred for 30 minutes before the addition of H-(D)-Ala-OBn-TsOH (1 eq, 85.38 mmol, 30 g) and triethyamine (2.2 eq, 187.84 mmol, 26.2 ml). After 1 hour at room temperature, the reaction mixture is quenched with water (300 ml) and extracted with DCM (2×200 ml). Combined organic layer was washed with water (100 ml), 1M HCl, and brine (50 ml) before dried over anhydrous Na$_2$SO$_4$. Solvent was evaporated in vacuum to give 35.41 g of crude material.

To a solution of crude material (35.41 g) in EtOAc (280 ml) was added 1M HCl in EtOAc (8 eq). The mixture was stirred for 5 hours before the addition of MTBE (300 ml) and the solid was filtered and washed with MTBE to give 22.91 g (90.84%) of desired product after dried under house vacuum overnight: m/z (ES+) 277.33

Example 5

Preparation of H-His(HCl)-Pro-(D)-Ala-OBn (7)

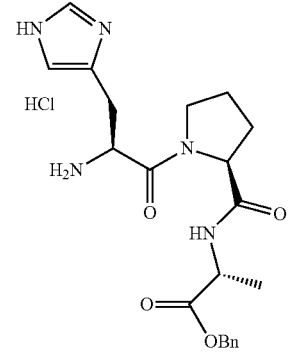

7

To a solution of Boc-His-OH (1.2 eq, 7.67 mmol, 1.96 g) in DMF (20 ml) was added both DCC 1.32 eq, 8.44 mmol, 1.74 g) and HOBt (1.32 eq, 8.44 mmol, 1.14 g) at room temperature. The reaction mixture was stirred for 3 hours before the addition of HCl-Pro-(D)Ala-OBn salt (1 eq, 6.39 mmol, 2 g) followed by Et$_3$N (2 eq, 12.78 mmol, 1.8 ml). After 3 hours, DCU was filtered and washed the cake with EtOAc. The filtrate was extracted with water, brine, dried, and concentrated under reduce pressure to give 3.59 g of crude product as a white solid (Boc-His-Pro-(D)-Ala-OBn); m/z (ES+) 514.48

EtOAc (45 ml) was added to the crude material than followed by 1M HCl in EtOAc (5 eq) to produce H-His(HCl)-Pro-(D)-Ala-OBn. The reaction mixture was stirred for 5 hours before filtered under nitrogen and washed with EtOAc. Dried under high vacuum at room temperature for overnight to give 3.03 g (94% overall yield): (HPLC Purity=92%)); m/z (ES+) 414.48.

Example 6

Preparation of Cbz-Sar-Arg(NO$_2$)—OH (8)

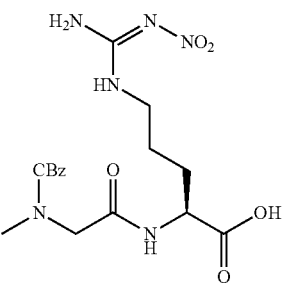

8

Pyridine (1.1 eq, 49.3 mmol, 3.97 ml) and pentafluorophenyl trifluoroacetate (1.2 eq, 53.8 mmol, 9.24 ml) were added to a solution of CBz-Sar-OH (10.0 g, 44.8 mmol) in DCM (120 ml) at 0° C. The reaction mixture was allowed to warm to room for 2 hours then quenched with sat. NH$_4$Cl (70 ml), water (2×70 ml), brine, dried over Na₂SO₄, and concentrated under reduced pressure to provide Z-Sar-OPfp in quantitative yield.

A solution of L-Arg(NO₂)—OH (0.9 eq, 40.3 mmol, 8.84 g) in 60 ml of water was added to the crude product prepared above (in 235 ml of acetonitrile) at room temperature followed by Et₃N (2 eq, 80.6 mmol, 11.2 ml) and stirred overnight. The reaction mixture was concentrated in vacuum to remove acetonitrile then dissolved in 200 ml of 5% HCl and extracted with EtOAc (5×100 ml). The combined organic extracts were washed with brine and dried over Na₂SO₄. Concentrated under vacuum before switched to MeOH (60 ml) and slowly added to 1.5 L of MTBE while stirring to precipitate product. Filtered and dried at 40° C. to give 15.12 g of white powder (88.4%): (HPLC Purity=99.1%)); m/z (ES+) 425.42

Example 7

Preparation of Boc-Val-Tyr-Ile-His-Pro-(D)Ala-OBn

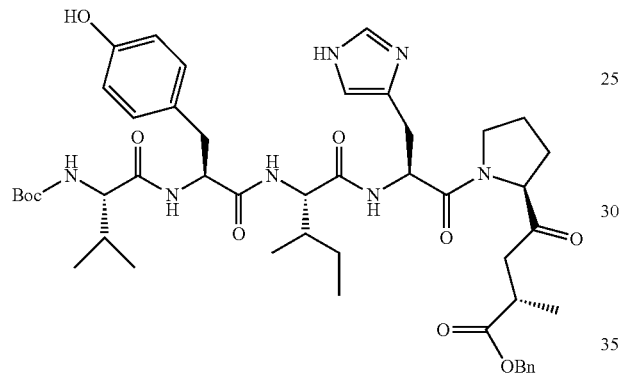

HATU (1 eq, 3.407 mmol, 1.295 g) was added to a solution of Boc-Val-Tyr-Ile-OH (1 eq, 3.4 mmol, 1.68 g) in 7 ml of DMF then followed by Et₃N (1 eq). The reaction mixture was stirred for 1 hour at room temperature.

In a separate vessel, H-His(HCl)-Pro-(D)-Ala-OBn (3.34 mmol, 1.5 g) in 15 ml of DCM, trimethylsilylchloride (2.1 eq, 7.01 mmol, 0.89 ml)) and TEA (3.5 eq, 11.69 mmol, 1.63 ml) are refluxed in DCM for 2.5 hours. The resulting solution is cooled and added to the reaction mixture prepared above at 0° C. The solution was stirred for 15 hours. The reaction was quenched with 5% HCl and stirred at room temperature for 30 minutes. Layers were separated; aqueous layer was extracted with EtOAc (2×30 ml). Combined organic extract was washed with water, brine and dried over anhydrous Na₂SO₄. Solvent was evaporated in vacuum, and dissolved in warm EtOAc. Crystallization on cooling to provide 2.11 g (71%) after filtration and dried overnight: (HPLC Purity=100%)); m/z (ES+) 890.07

Example 8

Preparation of Z-Sar-Arg(HCl)-Val-Tyr-Ile-His-Pro-(D)-Ala-OBn

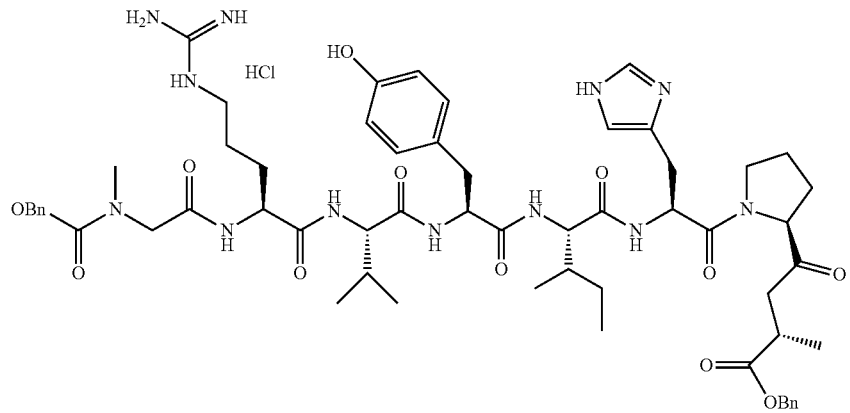 [SMILES: CCC(C)[C@H](NC(=O)[C@H](Cc1ccc(O)cc1)NC(=O)[C@@H](NC(=O)[C@H](CCCNC(=N)N)NC(=O)CN(C)C(=O)OCc1ccccc1)C(C)C)C(=O)N[C@@H](Cc1c[nH]cn1)C(=O)N1CCC[C@H]1C(=O)C[C@H](C)C(=O)OCc1ccccc1 ; Cl]

One equivalent of HCl in EtOAc was added to a solution of Z-Sar-Arg-OH (100 mg, 0.264 mmol) in 2 ml of DMF then followed by DCC (1 eq) and HOBt (1 eq) at room temperature. The reaction mixture was stirred for 1 hour.

In a separate vessel, H-Val(HCl)-Tyr-Ile-His-Pro-(D)Ala-OBn (1 eq, 0.264 mmol, 218 mg), trimethylsilylchloride (3.1 eq, 0.82 mmol, 0.104 ml)) and TEA (4 eq, 1.06 mmol, 0.148 ml) are refluxed in DCM (1.5 ml) for 2.5 hours. To this reaction mixture, activated Z-Sar-Arg-OH prepared above was added at 0° C. The solution was stirred for 16 hours. The reaction was quenched with 5% HCl and stirred at room temperature for 30 minutes. Layers were separated; aqueous layer was extracted with EtOAc/THF 1:1 (2×5 ml). Combined organic extract was dried ($Na_2SO_4$). Solvent was evaporated in vacuum, and subjected for reverse phase column chromatography to provide 128 mg (41%): (HPLC Purity=100%)); m/z (ES+) 1151.36

Example 9

Preparation of SEQ ID NO: 1-AcOH (TRV027-AcOH)

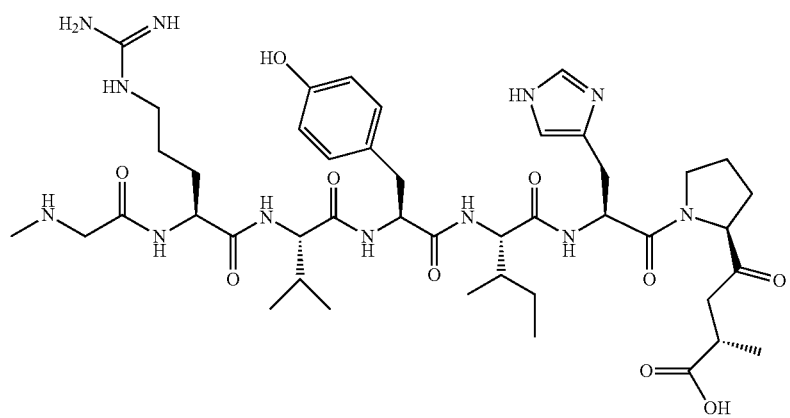 [SMILES: CCC(C)[C@H](NC(=O)[C@H](Cc1ccc(O)cc1)NC(=O)[C@@H](NC(=O)[C@H](CCCNC(=N)N)NC(=O)CNC)C(C)C)C(=O)N[C@@H](Cc1c[nH]cn1)C(=O)N1CCC[C@H]1C(=O)C[C@H](C)C(=O)O]

To a solution of Z-Sar-Arg(HCl)-Val-Tyr-Ile-His-Pro-(D)Ala-OBn (0.52 g, 0.438 mmol) in 2 ml of MeOH was added AcOH (10 eq) and 20 mg of $Pd(OH)_2$ then flushed with $H_2$ (3×) before hydrogenation overnight via $H_2$ balloon. Filtered and washed with MeOH before concentration to dryness. Water (2 ml) was added and extracted with EtOAc. The aqueous layer (2 ml) was warmed to 50° C. before cooling. Product was filtered and dried overnight to give 391 mg of product as a white solid: (HPLC Purity=100%)); m/z (ES+) 926.09

Example 10

Preparation of Z-Sar-Arg($NO_2$)-Val-Tyr-Ile-OH (9)

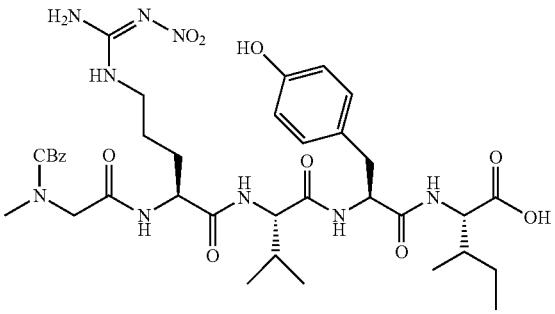

9

To a solution of Z-Sar-Arg($NO_2$)—OH (0.395 g, 0.932 mmol) in 5 ml of DMF was added DCC (1 eq, 0.932 mmol, 192 mg) and HOBt (1 eq, 0.932 mmol). The reaction mixture was stirred for 1 hour before the addition of Val(HCl)-Tyr-Ile-OH (1.02 eq, 0.951 mmol, 408 mg) and $Et_3N$ (3 eq, 2.853 mmol, 0.4 ml). The reaction mixture was left overnight before quenched with 5% HCl (5 ml) and extracted with EtOAc (3×10 ml). Combined organic extract was dried over anhydrous $Na_2SO_4$. Solvent was evaporated in vacuum, and dissolved in minimum amount of MeOH. Crystallization on cooling with the addition of EtOAc (as anti-solvent) to provide 603 mg (81%) after filtration and dried overnight: (HPLC Purity=97.1%)); m/z (ES+) 800.89

Example 11

Preparation of Z-Sar-Arg(NO₂)-Val-Tyr-Ile-His-Pro-(D)Ala-OBn (10)

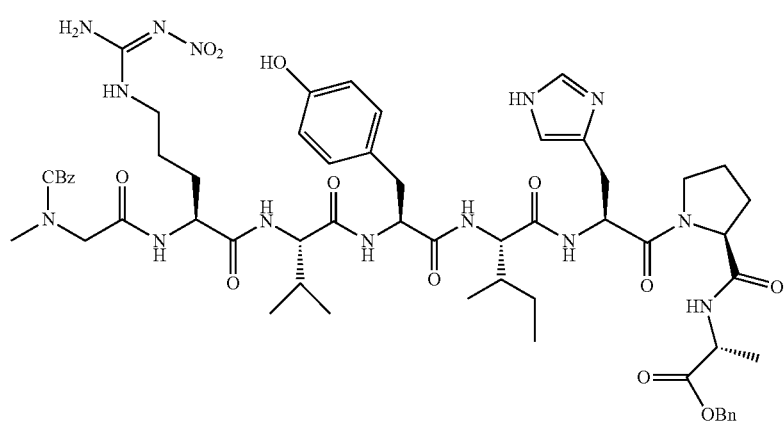

10

To a solution of Z-Sar-Arg(NO₂)-Val-Tyr-Ile-OH (0.5 g, 0.626 mmol) in 3 ml of DMF was added DCC (1 eq, 0.626 mmol, 129 mg) and HOBt (1 eq, 0.626 mmol, 102 mg). The reaction mixture was stirred for 2 hour before the addition of H-His(HCl)-Pro-(D)-Ala-OBn (1.2 eq, 0.751 mmol, 338 mg) and Et₃N (2.5 eq, 1.88 mmol, 0.26 ml). The reaction mixture was left overnight before quenched with water (5 ml) and extracted with EtOAc (3×10 ml). Combined organic extract was dried over anhydrous Na₂SO₄. Solvent was evaporated in vacuum, and dissolved in minimum amount of MeOH. Crystallization on cooling with the addition of EtOAc (as anti-solvent) to provide 381 mg (51%) after filtration and dried overnight: (HPLC Purity=98.4%)); m/z (ES+) 1196.35

Example 12

Preparation of Z-Sar-Arg(BisCBz)-OH

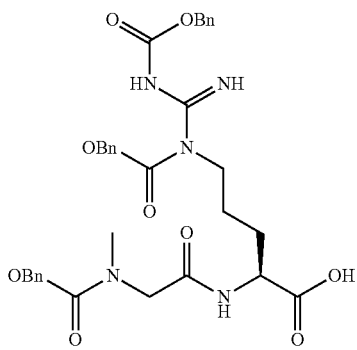 [SMILES: CN(CC(=O)N[C@@H](CCCN(C(=N)NC(=O)OCc1ccccc1)C(=O)OCc1ccccc1)C(=O)O)C(=O)OCc1ccccc1]

A slurry of Z-Sar-Arg-OH (1.0 eq, 0.35 mmol, 133 mg) in DCM (6.6 ml) was cooled to 0-5° C. and treated with DIPEA (8 eq, 2.8 mmol, 0.49 ml) and TMSCl (4 ea, 1.4 mmol, 0.18 ml). A clear solution was formed while stirring the reaction mixture at 0-5° C. for 30 minutes. Benzyl chloroformate (3.5 eq, 1.2 mmol, 0.17 ml) was then added dropwise during 5-10 minutes period. The mixture was allowed to warm to room temperature and left with stirring at RT for 30 minutes as LC/MS analysis showed the formation of desired product. It was then quenched with cold 1N HCl (20 ml). Layers were separated; aqueous layer was extracted with DCM (20 ml). Combined organic extract was washed with water (20 ml) and brine (20 ml) and then dried over anhydrous Na₂SO₄. It was concentrated under reduced pressure to a residue and subjected to a normal phase Combiflash chromatography (60% EA in Hexanes) to provide 203 mg (89%) of white solid [HPLC Purity=98.52%; m/z (ES+) 647.80]. The structure of the product was further confirmed by proton NMR analysis.

Example 13

Preparation of Boc-His(Bom)-Pro-(D)Ala-OBn

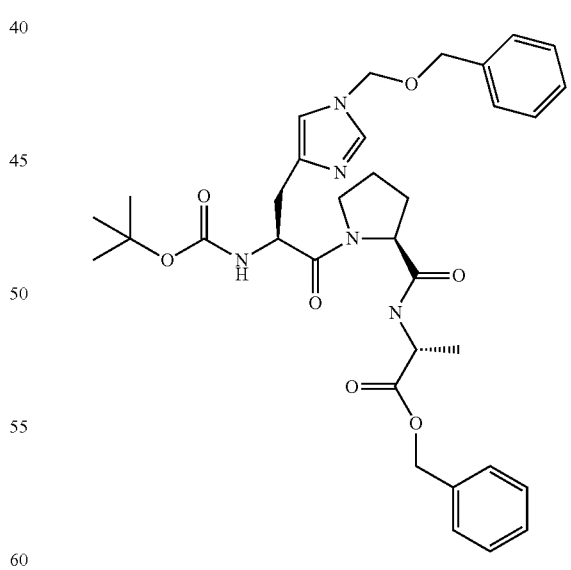

To a mixture of BocHis(Bom)OH, H2N-Pro-D-Ala-OBn.HCl and TEA in DMF was added HATU. The mixture was stirred for 2 h. The reaction mixture was diluted with dichloromethane and washed with water. Product was purified using reverse phase chromatography to give BocHis(Bom)-Pro-D-Ala-OBn as a white solid. m/z (ES+) 633.

Example 14

H₂N-His(Bom)-Pro-D-Ala-OBn

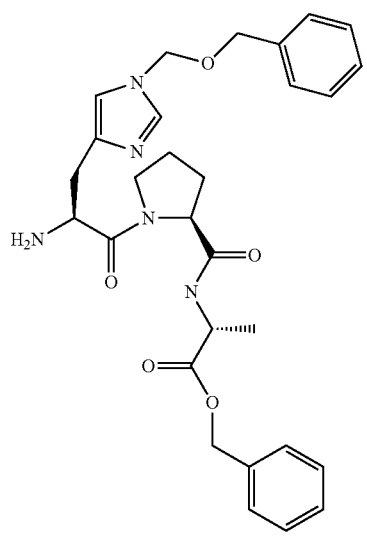 [SMILES: C[C@@H](NC(=O)[C@@H]1CCCN1C(=O)[C@@H](N)Cc1cn(COCc2ccccc2)cn1)C(=O)OCc1ccccc1]

A solution of BocHis(Bom)-Pro-D-Ala-OBn in dioxanes containing HCl (4N) was stirred for 16 h. The mixture was concentrated in vacuo. The residue was redissolved in warm chlorobenzene and cooled to crystallize the product as the HCl salt. A small portion was purified by reverse phase HPLC to give H₂N-His(Bom)-Pro-D-Ala-OBn·HOOCCF₃ as a white solid. m/z (ES+): 533 (M+1).

Example 15

Preparation of FmocHis(Trt)-Pro-D-Ala-OBn

To a mixture of FmocHis(Trt)OH, H2N-Pro-D-Ala-OBn·HCl and TEA in DMF was added HATU. The mixture was stirred for 2 h. The reaction mixture was diluted with dichloromethane and washed with water. Product was purified using reverse phase chromatography to give FmocHis(Trt)-Pro-D-Ala-OBn as a white solid.

Example 16

Preparation of SEQ ID NO: 1 (Formula 1)

SEQ ID NO: 1 was prepared according to Scheme 1 (FIG. 1).

SEQ ID NO: 1 was also prepared according to Scheme 2 (FIG. 2):

Example 17

Preparation of Formula 1A. A Compound of Formula 1A is Prepared According to Scheme 3 (FIG. 3)

While the embodiments have been depicted and described by reference to exemplary embodiments, such a reference does not imply a limitation on the scope, and no such limitation is to be inferred. The embodiments are capable of considerable modification, alteration, and equivalents in form and function, as will occur to those ordinarily skilled in the pertinent arts having the benefit of this disclosure. All references cited herein are hereby incorporated by reference in their entirety.

---

What is claimed is:

1. A method of preparing

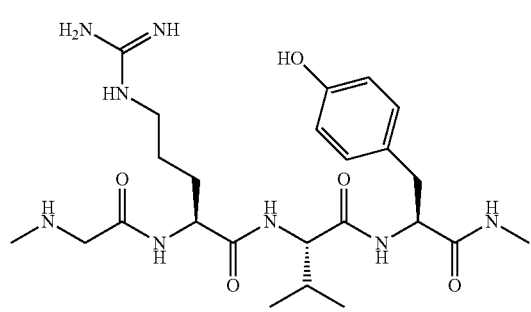

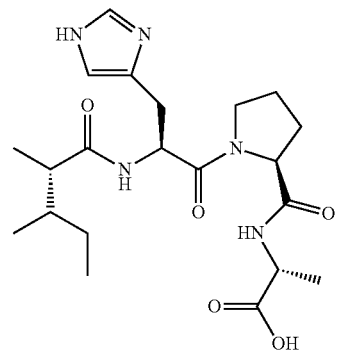

or a pharmaceutically acceptable salt thereof, solvate, or hydrate thereof, the method comprising, a) contacting H-His(HCl)-Pro-(D)-Ala-OR$_4$ with Z-Sar-Arg(NO$_2$)-Val-Tyr-Ile-OH under conditions sufficient to produce Z-Sar-Arg(NO$_2$)-Val-Tyr-Ile-His-Pro-(D)-Ala-OR$_4$; and
b) hydrogenating Z-Sar-Arg(NO$_2$)-Val-Tyr-Ile-His-Pro-(D)-Ala-OR$_4$ to produce

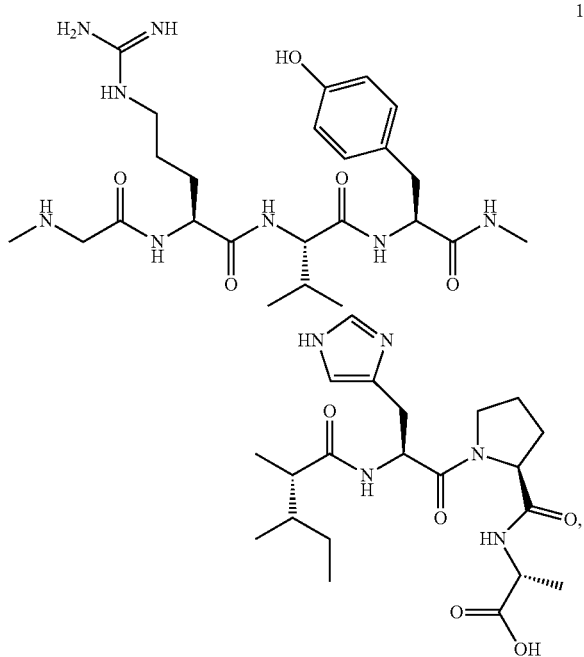

wherein
Z is carboxybenzyl; and
R$_4$ is H, Me, Et, tert-Bu, Bn, TMS or other carboxylic acid protecting group.

2. The method of claim 1 further comprising preparing H-His(HCl)-Pro-(D)-Ala-OR$_4$, the method comprising:
contacting H-Pro(acid)-(D)-Ala-OR$_4$ with activated Boc-Histidine to form Boc-His-Pro-D-Ala-OBn, followed by deprotection in the presence of a suitable acid to produce H-His(HCl)-Pro-(D)-Ala-OR$_4$,
wherein:
R$_4$ is H, Me, Et, tert-Bu, Bn, TMS or other carboxylic acid protecting group.

3. The method of claim 1 further comprising preparing R$_1$-Val-Tyr-Ile-OH, the method comprising:
contacting R$_3$-Val-OH with Tri-TMS-Tyr under conditions sufficient to produce R$_3$-Val-Tyr-OH; and
contacting R$_3$-Val-Tyr-OH with Di-TMS-Ile under conditions sufficient to produce R$_1$-Val-Tyr-Ile-OH,
wherein R$_3$ and R$_1$ are, independently, a nitrogen protecting group.

4. The method of 3, further comprising preparing H-Val(HCl)-Tyr-Ile-OH, the method comprising treating R$_1$-Val-Tyr-Ile-OH with HCl to produce H-Val(HCl)-Tyr-Ile-OH.

5. The method of claim 1 further comprising preparing Z-Sar-Arg(NO$_2$)—OH, the method comprising contacting Z-Sar-OH with H-Arg(NO$_2$)—OH under conditions sufficient to produce Z-Sar-Arg(NO$_2$)—OH, wherein Z is carboxybenzyl.

6. The method of claim 1, wherein R$_4$ is H, Me, Et, tert-Bu, Bn, or TMS.

7. The method of claim 1, wherein R$_4$ is Bn.

8. The method of claim 2, wherein the suitable acid is HCl.

9. The method of claim 3, wherein the nitrogen protecting group is selected from the group consisting of Cbz, Fmoc, Boc, Alloc, and TFA.

10. The method of claim 3, wherein R$_1$ is Cbz.

11. The method of claim 3, wherein R$_3$ is Cbz.

12. The method of claim 3, wherein R$_1$ and R$_3$ are different nitrogen protecting groups.

* * * * *